US 9,119,812 B2

(12) United States Patent
Jin et al.

(10) Patent No.: US 9,119,812 B2
(45) Date of Patent: Sep. 1, 2015

(54) INFLUENZA HEMAGGLUTININ AND NEURAMINIDASE VARIANTS

(71) Applicants: MEDIMMUNE, LLC, Gaithersburg, MD (US); The United States of America, National Institutes of Health, Washington, DC (US)

(72) Inventors: Hong Jin, Cupertino, CA (US); Xing Cheng, Sunnyvale, CA (US); Kanta Subbarao, Washington, DC (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/086,902

(22) Filed: Nov. 21, 2013

(65) Prior Publication Data

US 2014/0079726 A1    Mar. 20, 2014

Related U.S. Application Data

(62) Division of application No. 12/699,108, filed on Feb. 3, 2010, now Pat. No. 8,613,935.

(60) Provisional application No. 61/152,094, filed on Feb. 12, 2009.

(51) Int. Cl.
*A61K 39/145* (2006.01)
*C12N 7/00* (2006.01)
*A61K 39/00* (2006.01)

(52) U.S. Cl.
CPC .............. *A61K 39/145* (2013.01); *C12N 7/00* (2013.01); *A61K 2039/5254* (2013.01); *A61K 2039/5258* (2013.01); *C12N 2760/16134* (2013.01)

(58) Field of Classification Search
None
See application file for complete search history.

(56) References Cited

U.S. PATENT DOCUMENTS

| | | |
|---|---|---|
| 3,992,522 A | 11/1976 | Chanock et al. |
| 4,071,618 A | 1/1978 | Konobe et al. |
| 4,634,666 A | 1/1987 | Engleman et al. |
| 4,659,569 A | 4/1987 | Mitsuhashi et al. |
| 4,752,473 A | 6/1988 | Nayak et al. |
| 5,166,057 A | 11/1992 | Palese et al. |
| 5,665,362 A | 9/1997 | Inglis et al. |
| 5,690,937 A | 11/1997 | Parkin |
| 5,716,821 A | 2/1998 | Wertz et al. |
| 5,756,341 A | 5/1998 | Kistner et al. |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,922,326 A | 7/1999 | Murphy |
| 6,001,634 A | 12/1999 | Palese et al. |
| 6,033,886 A | 3/2000 | Conzelmann |
| 6,090,391 A | 7/2000 | Parkin |
| 6,146,642 A | 11/2000 | Garcia-Sastre et al. |
| 6,146,873 A | 11/2000 | Kistner |
| 6,168,943 B1 | 1/2001 | Rose |
| 6,951,754 B2 | 10/2005 | Hoffmann |
| 7,037,707 B2 | 5/2006 | Webster et al. |
| 7,459,162 B2 | 12/2008 | Yang et al. |
| 7,504,109 B2 | 3/2009 | Yang et al. |
| 7,527,800 B2 | 5/2009 | Yang et al. |
| 7,744,901 B2 | 6/2010 | Yang et al. |
| 8,039,002 B2 | 10/2011 | Yang |
| 8,084,594 B2 | 12/2011 | Gramer et al. |
| 8,431,137 B2 | 4/2013 | Yang et al. |
| 2002/0119445 A1 | 8/2002 | Parkin et al. |
| 2002/0164770 A1 | 11/2002 | Hoffmann |
| 2003/0035814 A1 | 2/2003 | Kawaoka |
| 2003/0147916 A1 | 8/2003 | Ferko |
| 2004/0029251 A1 | 2/2004 | Hoffman |
| 2004/0137013 A1 | 7/2004 | Katinger |
| 2005/0042229 A1 | 2/2005 | Yang |
| 2005/0266026 A1 | 12/2005 | Hoffmann |
| 2005/0287172 A1 | 12/2005 | Yang et al. |
| 2006/0008473 A1 | 1/2006 | Yang et al. |
| 2008/0057081 A1 | 3/2008 | Yang et al. |
| 2008/0069821 A1 | 3/2008 | Yang et al. |
| 2009/0175898 A1 | 7/2009 | Yang et al. |
| 2009/0175909 A1 | 7/2009 | Yang et al. |
| 2010/0330118 A1 | 12/2010 | Jin et al. |
| 2011/0052618 A1 | 3/2011 | Yang et al. |
| 2011/0182936 A1 | 7/2011 | Yang |
| 2012/0009215 A1 | 1/2012 | Yang |
| 2012/0034264 A1 | 2/2012 | Yang et al. |

FOREIGN PATENT DOCUMENTS

| | | |
|---|---|---|
| EP | 0702085 | 3/1996 |
| EP | 0863202 | 9/1998 |
| EP | 0864645 | 9/1998 |
| EP | 0780475 | 6/1999 |
| EP | 1826269 | 8/2007 |
| JP | 2004-500842 | 1/2004 |
| RU | 2 315 101 | 1/2008 |
| WO | WO 91/03552 | 3/1991 |
| WO | WO 93/21306 | 10/1993 |
| WO | WO 96/10632 | 4/1996 |
| WO | WO 96/34625 | 11/1996 |

(Continued)

OTHER PUBLICATIONS

Sequence alignment of instant SEQ ID No. 7 with SEQ ID No. 3 (Geneseq database access No. AWF81563) of Gramer et al., effective priority to provisional applications filed in 2007.*

(Continued)

*Primary Examiner* — Shanon A Foley
(74) *Attorney, Agent, or Firm* — Grant IP, Inc.

(57) ABSTRACT

Polypeptides, polynucleotides, reassortant viruses, immunogenic compositions and vaccines comprising influenza hemagglutinin and neuraminidase variants and method using thereof are provided.

20 Claims, 4 Drawing Sheets

(56) References Cited

FOREIGN PATENT DOCUMENTS

| WO | WO 97/06270 | 2/1997 |
|---|---|---|
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/53786 | 9/2000 |
| WO | WO 00/60050 | 10/2000 |
| WO | WO 01/83794 | 11/2001 |
| WO | WO 03/075955 | 9/2003 |
| WO | WO 03/091401 | 11/2003 |
| WO | WO 2005/116258 | 8/2005 |
| WO | WO 2005/116260 | 8/2005 |
| WO | WO 2008/021959 | 2/2008 |
| WO | WO 2009/014919 | 1/2009 |
| WO | WO 2010/093537 | 8/2010 |

OTHER PUBLICATIONS

Instant SEQ ID No. 8 sequence alignment with UniProt database access No. A9YN73_9INFA Feb. 2008.*
Office Action mailed on Jul. 7, 2014 in U.S. Appl. No. 13/784,259, filed Mar. 4, 2013 and published as US 2013-0189293 on Jul. 25, 2013.
Uniprot Accession No. Q693C8, published Sep. 13, 2004, hemagglutinin, Influenza A virus (A/chicken/British Columbia/GSC_human_B/04(H7N3)).
Uniprot Accession No. Q6DSV6, published Aug. 16, 2004, hemagglutinin, Influenza A virus (A/GSC_chicken_B/British Columbia/04(H7N3)).
Uniprot Accession No. Q693C5, published Sep. 13, 2004, hemagglutinin, Influenza A virus (A/chicken/British Columbia/GSC_human_B/04(H7N3)).
Uniprot Accession No. Q6DQJ4, published Aug. 16, 2004, hemagglutinin, Influenza A virus (A/GSC_chicken_B/British Columbia/04(H7N3)).
Attwood, T. The Babel of Bioinformatics, Science (2000) vol. 290, No. 5491, pp. 471-473.
Baker et al., Protein Structure Predication and Structural Genomics, Science (2001) vol. 294, No. 5540, pp. 93-96.
Banerjee and Barik. 1992.—Gene expression of vesicular stomatitis virus genome RNN. Virology. 188):417-28.
Baron and Barrett, 1997,—Rescue of Rinderpest Virus from Cloned eDNA, J. Virol. 71 :1265-1271.
Basler et al., 1999, "Mutation of Neuraminidase Cysteine Residues Yields Temperature-Sensitive Infuenza Viruses", J. of Virology 73(10):8095-8103.
Beare et al., 1975, "Trials in Man with live Recombinants Made from AJPRI8/34 (HO N1) and Wild H3 N2 Influenza Viruses", Lancet 729-732.
Belshe et al., 1998, The efficacy of live attenuated, cold-adapted, trivalent, intranasal influenza virus vaccine in children: N Engl J Med 338:1405-12.
Belshe, 1995 "A Review of Attenuation of Influenza Viruses by Genetic manipulation", American Journal of Respiratory and Critical Care Medicine 152:S72-S75.
Bender et al., 1999, "Characterization of the surface proteins of influenza A (H5N1) viruses." Virology 254(1 ):115-23.
Bergmann, et al., 1995, "The relative amount of an influenza A virus segment present in the viral particle is not affected . . . ", J. of Gen. Virology, 76:3211-3215.
Boyce at al., 2000, "Safety and immunogenicity of adjuvanted and unadjuvantad subunit influenza vaccines administered intranasally 10 healthy adults", Vaccine 19:217-226.
Boyer et al., 1994, "Infectious transcripts and cDNAclones of RNA viruses", Virology. 198:415-26.
Brandt et al.. 2001, Molecular Determinants of Virulence, Cell Tropism, and Pathogenic Phenotype of Infectious Bursal Disease Virus; Journal of Virology 75(24); 11974-11982.

Brigden and Elliott, 1996, Rescue of a Segmented Negative-Strand RNA Virus Entirely from Cloned Complementary DNAS., Proc. Natl. Acad. Sci. USA 93:15400-15404.
Buchholz et al., 1999 "Generation of Bovine Resp. Syncytial Virus (BRSV) from cDNA: BRSV NS2 Is Not Essential for Virus Replication in Tissue Culture . . . " J. Virol. 73:251-259.
Bukreyev et al., 1996, "Recovery of infectious respiratory syncytial virus expressing an additional, foreign gene", J Viral. 70(10):6634-41.
Castrucci et al., 1995, "Reverse genetics system. for generation of an influenza A virus mutant containing a deletion of the carboxyl-terminal M2 .. ", J Virol. 69(5):2725-28.
Chen et al., 1999, "Influenza A virus NS1 protein targets poly (A)-binding protein II of the cellular 3'-end processing machinery", EMBO 18: 2273-2283.
Chen et al, "Saftey, immunogenicity, and efficacy of cold-adapted A/Ann Arbor/6/60 (H2N2) vaccine in mice and ferrets", Virology, Elsevier, Amsterdam, NL, vol. 398, No. 1, Mar. 1, 2010, pp. 109-114.
Clarke et al., 2000, "Rescue of mumps virus from cDNAJ", J Virol. 74 (10):4831-38.
Collins et al., 1996, "Parainfluenza Viruses", Fields Virology. Lippincott-Raven Publishers, Phi/a., pp. 1205-1241.
Collins et al., 1995, "Production of infectious human respiratory syncytial virus from cloned cDNA confirms an essential role . . . " PNAS 92: 11563-1567.
Collins et al.. 1991, "Rescue of Synthetic Analogs of Respiratory Syncytial Virus Genomic RNA and Effect of Truncations.", Proc. Nail. Acad. Sci. USA 88:9663-9667.
Conzelmann et al., 1994. "Rescue of synthetic genomic RNA analogs of rabies virus by plasmid-encoded proteins", J Virol. 68(2):713-19.
Conzelmann et al , 1998. "Nonsegmented negative-strand RNA viruses: genetics and manipulation of viral genomes", Annu Rev Genet. 32:123-162.
Conzelmann et al ., 1996. "Genetic engineering of animal RNA viruses", Trends Microbiol. 4(10):386-93.
Conzelmann. 1996. "Genetic manipulation of non-segmented negative-strand RNA viruses", J Gen Virol. 77 (Pt 3):381-89.
Cox, at al.; "Identification of Sequence Changes in the Cold-Adapted, Live Attenuated Influenza Vaccine Strain, A/Ann *Arbor/6/60* (H2N2)," Virology, 1988; 167: 554-567.
Database EMBL [Online] E.B.I. Hinxtoin U.K.; Nov. 1, 1999, Bender C et al: "Hemagglutinin (Fragment).", Database accession No. Q9WDG1.
Database EMBL [Online] E.B.I. Hinxton U.K., Jan. 15, 2008, Kaverin NV et al., "Hemagglutinin" XP002684322, Database Accession No. A8UDQ2.
Database EMBL [Online] E.B.I. Hinxton U.K.; May 1, 2000, Hiromoto Y et al: "Hemagglutinin (Fragment).", Database accession No. Q9QSJ8.
Database EMBL [Online] E.B.I. Hinxton U.K.; Nov. 1, 1999, Bender C et al: "Hemagglutinin (Fragment).", Database accession No. Q9WDF7.
Database Geneseq [Online} Mar. 9, 2006, "Hemaglutinin, SEQ ID 1345." XP002712609, retrived from EBI accession No. GSP:AEF02090 Database accession No. AEF02090.
De and Banerjee, 1985. "Requirements and Functions of Vesicular Stomatitis Virus L . and NS Proteins in the Transcription .." , Biochem. & Biophys. Res. Commun. 126:40-49.
De and Banerjee, 1993. "Rescue of synthetic analogs of genome RNA of human parainfluenza virus type 3", Virology. 96:344-48.
De and Banerjee, 1994, "Reverse genetics of negative strand RNA viruses," Indian J Biochem & Biophys. 31:367-76.
De et al., "Complete sequence of a cDNA clone of the hemagglutinin gene of influenza AlChickenlScotiandl59 (H5NI) virus: comparison with contemporary North American and European strains", Nucleic Acids Research, 1988. vol. 16, No. 9, pp. 4181-4182.
De et al., "Protection against virulent H5 avian influenza virus infection in chickens by an inactivated vaccine produced with recombinant vaccine virus", Jun. 1988, Vaccine, vol. 6, pp. 257-261.
De La Luna et al., 1995, "Influenza virus NS1 Protein Enhances the Rate of Translation Initiation of Viral mRNAs", J. ofVirol. 69: 2427-2433.

(56) References Cited

OTHER PUBLICATIONS

De la Luna et al.. 1993. Influenza virus naked RNA can be expressed upon transfection into cells co-expressing the three subunits . . . n J. Gen.Virol. 74: 535-39.
Development of a vaccine effective against avian influenza H5N1 infection in humans. RelevéÉpidémiologique Hebdomadaire / Section D'Hygiéne Du Secrétariat De La Société Des Nations = Weekly Epidemiological Record / Health Section of the Secretariat of the League of Nations Jan. 23, 2004, vol. 79, No. 4, Jan. 23, 2004, pp. 25-26.
Dimock et al., 1993, "Rescue of synthetic analogs of genomic RNA and replicative-intermed. RNA of human parainfluenza virus type 3,", J Virol. 67(5):2772-78.
Dreher and Hall, 1988, "Mutational Analysis of the Sequence and Structural Requirements in Brome Mosaic Virus RNA for Minus Strand Promoter Activity", J. Mol. Biol. 201 :31-40.
Dreher et at, 1984, "Mutant Viral RNAs Synthesized in vitro Show Altered Aminoacylation and Replicase Template Activities", Nature 311 :171-175.
Dunn et al., 1995, "Transcription of a recombinant bunyavirus RNA template by transiently expressed bunyavirus proteins", Virology, 211 :133-43.
Durbin et al., 1997, "Recovery of infectious Human Parainfluenza Virus Type 3 fram cDNA", Viral. 235:323-332.
Edwards et al., 1994. "A randomized controlled trial of cold adapted and inactivated vaccines for the prevention of influenza a disease", J Infect Dis 169:68-76.
Edwards, et al., "Saftey and immunogenicity of live attenuated cold adapted influenza B/Ann Arbor/1/86 reassortant virus vaccine in infants and children," J. Infect Dis. Apr. 1991; 163(4):740-745.
Egorov et al., 1998. "Transfectant Influenza A Viruses with Long Deletions in the NS1 Protein Grow Efficiently in Vero Cells", J. of Virology 72(8):6437-6441.
Elliot et al., 1997, Abstract # 96 10.sup.th International conference on Negative Strand Viruses.
Elliott et al., 1991, "Some highlights of virus research in 1990", J Gen Virol. 72:1761-79. Review.
Emerson and Yu, 1975, "Both NS and L Proteins are Required for in vitro RNA Synthesis by Vosicular Stomatitis Virus", J. Virol. 15:1348-1356.
Enami and Palese, 1991, "High-Efficiency Formation of Influenza Virus Transfectants", J. Virol. 65:2711-2713.
Enami et al., 1991, "An influenza virus containing nine different RNA segments", Virology. 185:291-98.
Enami et al, 2000. "Characterization of Influenza Virus NS1 Protein by Using a Novel Helper-Virus Free Reverse Genetic System", J. of Virology 74(12):5556-5561.
Enami et al., 1990, "Introduction of Site Specific Mutations into the Genome of Influenza Virus", Proc Natl Acad Sci USA 87: 3802-3805.
Extended European Search Report dated: Jan. 30, 2013 in European Application No. 12174997 filed on: May 20, 2005.
Extended European Search Report dated: May 16, 2012 in European Application No. 12159225 filed on: May 20, 2005.
Extended European Search Report dated: Oct. 11, 2012 in European Application No. 12172385 filed on: May 20, 2005.
Extended European Search Report dated: Sep. 25, 2013 in European Application No. EP10741567 filed: Feb. 3, 2010.
Fahey and Schooley, 1992, "Status of Immune-Based Therapies in HIV Infection and AIDS". Clin. Exp. Immunol. 88:1-5.
Flandorfar at al., 2003, ●Chimeric Influenza A Viruses with a Functional Influenza B Virus Neuraminidase or Hemagglutinin, J. of Virology 77(17):9116-9123.
Flick, et al, "Promoter elements in the influenza vRNA terminal structure," RNA, 1996; 2(10):1046-1057.
Fodor et al., 1999, "Rescue of Influenza A Virus from Recombinant DNA", J. of Virology 73(11):9679-9682.
Fortes et al., 1994, "Influenza virus NS1 protein inhibits pre-mRNA splicing and blocks mRNA nucleocytoplasmic transport". EMBO J. 13: 704-712.
Fourchier et al., "Avian Influenza a Virus (H7N7) associated with Human conjunctivitus and a fatal case of acute respiratory distress syndrome," PNAS, Feb. 3, 2004;101(5):1356-1361.
Furminger, "Vaccine Production", Textbook of Influenza, pp. 324-332; (1996).
Garcia-Sastre A, Palese P, 1993. "Genetic manipulation of negative-strand RNA virus genomes", Annu Rev Microbiol. 47:765-90.
Garcin et al., 1995. "A highly recombinogenic system for the recovery of infectious sendai paramyxovirus from cDNA: generation of a noveL" EMBO J. 14: 6087-6094.
Genbank Accession # AAW80717, hemagglutinin HA [Influenza A virus (ANiet Nam/1203/2004 (H5N 1 ))], published Feb. 9, 2005.
Genbank Accession# AAF74325, published Jun. 7, 2000.
GenBank Accession# AAW80723.1, published: Feb. 9, 2005.
GenBank Accession# AF046080.1, published: May 17, 2005.
GenBank Accession# AF046097. 1, published , May 17, 2005.
Genebank Accessino No. AF250479.1, Jul. 25, 2000, Influenza A virus (A/Teal/Hong Kong/W312/97(H6N1)) segment 4 hemagglutinin (HA) gene, complete cds.
GeneBank Accession No. AY553802, Influenza A virus (A/little grebe/Thailand/Phichit-01/2004(H5N1) hemag-glutinin (HA) gene, partial cds. May 21, 2004.
Genebank Accession No. AY651334, Li K S et al: "Influenza A virus (A/Viet Nam/1203/2004(H5N1)) hemagglutinin (HA) gene, partial cds." Jul. 19, 2004.
Genebank Accession No. AY651447, Li K S et al: "Influenza A virus (A/Viet Nam/1203/2004(H5N1)) neuraminidase (NA) gene, complete cds." Jul. 19, 2004.
GeneBank Accession No. CAC84240.1, Apr. 15, 2005, "haemagglutinin" [Influenza A virus (A/duck/Hong Kong/182/77 (H6N9))].
Genebank Accession No. CAC84982.1, Jan. 15, 2002, haemagglutinin [Influenza A virus (A/quail/Hong Kong/SF550/00(H6N1))].
Genebank Accession No. CACA21084860.1, Apr. 15, 2005, haemagglutinin [Influenza A virus (A/chukka/Hong Kong/FY295/00(H6N1))].
GeneBank Accession# L20407.1 Influenza A Virus (A/Japan/305-/1957(H2N2)) hemagglutinin (HA) gene, complete cds. [online] May 2, 2006 [retrieved Jul. 23, 2010]. Available on the internet, url: http://www.ncbi.nlm.nih.gov/nuccore/305154.
Ghendon, "Cold-Adapted, Live Influenza Vaccines Developed in Russia," Textbook of Influenza, Chapter 29, pp. 391-399. 1998.
Goto et al., 1997. "Mutations Affecting the Sensitivity of the I nfluenza Virus Neuraminidase to 4-Guanidino-2,4-Dideoxy-2,3 Oehydro-N-Acetyineuraminic Acid", Virol. 238:265-27.
Govorkova et al., "Lethality to ferrets of H5N1 influenza viruses isolated from humans and poultry in 2004" (Journal of Virology 79:2191-2198, Feb. 2005).
Govorkova, EA, et al., "African Green Monkey Kidney (Vero) Cells Provide an Alternative Host Cell," J. of Virology, Am. Soc. For Microbiology, Aug. 1996,70(8):5519-5524.
Grosfeld et al., 1995, RNA replication by respiratory syncytial virus (RSV) is directed by theN., P., and L proteins: transcription . . . J. Virol. 69(9):5677-5686.
Guan, Yi, et al., "Molecular Characterization of H9N2 Influenza Viruses: Were They the Donors of the "Internal" . . . ?", Proc. Natl. Acad. Sci., U.S.A. Aug. 1999,96:9363-9367.
Ha et al., H5 avian and H9 swine influenza virus haemagglutinin structures: possible origin of influenza subtypes, 2002, The EMBO Journal, vol. 21, No. 5, pp. 865-875.
Hatada and Fukudo, 1992. "Binding of influenza a virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Herlocher et al., "Sequence Comparisons of *AIAA16/60* Influenza Viruses: Mutations Which May Contribute to Attenuation", Virus Research, 42:11-25; (1996).
Hien et al., "Avian Influenza A (H5N1) in 10 Patients in Vietnam," The New England Journal of Medicine, vol. 350, No. 12, Mar. 18, 2004, pp. 1179-1188.
Hilleman Maurice R., 2000, "Vaccines in historic evolution and perspective: a narrative of vaccine discoveries", Vaccine 18: 1436-1447.

(56) References Cited

OTHER PUBLICATIONS

Hiromoto et al., "Evolutionary Characterization of the six internal genes of H5N1 human influenza A virus," Journal of General Virology, 81, pp. 1293-1303 (2000).

Hirst, M. et al., "Novel Avian Influenza H7N3 Strain Outbreak. British Columbia," Emerg Infet Dis. Dec. 2004;10(12):2192-2195.

Hoffman and Banerjee, 1997. "An Infectious Clone of Human Parainfluenza Virus Type 3", J. Virol. 71 :4272-4277.

Hoffman et al., "Eight-Plasmid Resue System for Influenza A Virus", International Congress Series, 1219:1007-1013; (2001).

Hoffman et al., 2002, "Rescue of influenza B virus from eight plasmids", PNAS 99: 11411-11416.

Hoffman et al.. "Ambisense" Approach for the Generation of Influenza A Virus: vRNA and mRNA Synthesis from One Template, Virology, 267:310-317; (2000).

Hoffman et al.. "Eight-Plasmid System for Rapid Generation of Influenza Virus Vaccines". Vaccine, 20:3165-3170; (2002).

Hoffmann et al., 2000 "Characterization of the Influenza A Virus Gene Pool in Avian Species in Southern China: Was H6N1 . . . ?" J. Virology, 74(14):6309-6315.

Hoffmann et al., 2005, "Role of specific hemaggluitnin amino acids in the immunogenicity." PNAS USA 102 (36) 12915-20. Epub Aug. 23, 2005.

Hoffmann et al."Universal primer set for Ille full-length amplification of all influenza A viruses." Arch Virol. Dec. 2001;146 (12):2275-89).

Hoffmann et al., 2000, "A DNA transfection system for generation of influenza A virus from eight plasmids", PNAS 97(11):6108-6113.

Hoffmann et al..2000, "Unidirectional RNA polymerase 1-polymerase II transcription system for the generation of influenza A virus . . . ", J.I of Gen. Virology 81':2843-2847.

Hoffmann, Erich, "Aufbau eines RNA-Polymerase I-Vektorsystems zur gezielten Mutagenese von Influenza A Viren", "Generation of an RNA-Polymerase Vector Syst. for the Select. Mutagenesis ..,"Gieben 1997 (Doctoral Dissertation of Sch. of Nat. Sciences, Justus Uebig U. Gieben with translation).

Huang et al., 1990, "Determination of Influenza virus proteins required for genome replication", J Virol. 64(11 ):5669-73.

International Search Report and Written Opinion mailed on: Jul. 7, 2008 in International application No. PCT/US05/017733 filed on May 20, 2005 and published as WO/2005/116260 on Aug. 12, 2005.

International Search Report and Written Opinion mailed on: Oct. 25, 2006, in International application No. PCT/US05/017729 filed on May 20, 2005, and published as: WO/2005/0116258 on: Aug. 12, 2005.

International Search Report mailed on: Jul. 30, 2010, in International application No. PCT/US10/22970 filed on Feb. 3, 2010.

Jin et al., "Multiple amino acid residues confer temperature sensitivity to human influenza virus vaccine strains (FluMist) derived from cold adapted A/Ann Arbor/6/60," Virology 306 (2003) 18-24.

Kaplan et al., 1985. "In vitro Synthesis of Infectious Poliovirus RNA", Proc. Natl. Acad. Sci. USA 82:8424-8428.

Katinger et al., Attenuated Influenza Virus as a Vector for Mucosal Immunization against HIV-1A, Vaccines, pp. 315-319. (1997).

Kato et al., 1996, Initiation of Sendai Virus Multiplication from Transfected cDNA or RNA with Negative or Positive Sensen Genes to Cells 1:569-579.

Kaverin et al., "Cross-protection and reassortment studies with avian H2 influenza viruses", Archives of Virology, vol. 145, No. 6, 2000, pp. 1059-1066.

Keitel, et al., "Live Cold-Adapted, Reassortant Influenza Vaccines (USA)," Textbook of Influenza, Chapter 28, pp. 373-390. 1998.

Kimura et al., 1992, "Transcription of a recombinant influenza virus RNA in cells that can express the influenza virus RNA polym~rase . . . ", J Gen Viral. 73:1321-28.

Kimura et al., 1993, "An in vivo study of the replication origin in the influenza virus complementary RNA", J Biochem (Tokyo) 113:88-92.

Kobayashi et al., 1992, Reconstitution of influenza virus RNA polymerase from three subunits expressed using recombinant baculovirus system. Virus Res. 22:235-45.

Konarska et al., 1990, "Structure of RNAs replicated by the DNA-dependent T7 RNA polymerase", Cell. 63(3):609-18.

Krystal et at, 1986, "Expression of the Three Influenza Virus Polymerase Proteins in a Single Cell Allows Growth . . . ", Proc. Natl. Acad. Sci. USA 83:2709-2713.

Kunkel, 1985, "Rapid and Efficient Site-Specific Mutagenesis without Phenotypic Selection", Proc. Natl. Acad. Sci. USA 82:468-.

Lamb et al., 1996, Fundamental Virology 3.sup.rd ed. Chapters 20 and 21.

Lawson et al., 1995, "Recombinant vesicular stomatitis viruses from DNA", Proc Natl Acad Sci U S A.92:4477-81.

Levis et al., 1986, "Deletion Mapping of Sindbis Virus 01 RNAs Derived from cDNAs Defines the Sequences Essential for Replication and Packaging", Cell 44:137-145.

Li et al., "Genesis of a highly pathogenic and potentially pandemic H5N1 influenza virus in eastern Asia" Nature, Nature Publishing Group, London, UK, vol. 430, No. 6996, Jul. 8, 2004, pp. 209-213.

Li et al., "Influenza A Virus (A/Viet Nam/1203/2004(H5N1) hemagglutinin (HA) gene, partial cds" EMBL, Jul. 19, 2004, XP002544221.

Li et al., "Influenza A Virus (A/VietNam/1203/2004(H5N1) neuraminidase (NA) gene, complete cds" EMBL, Jul. 19, 2004, XP002544220.

Li et al., 1999. Recombinant influenza A virus vaccines for the pathogenic human A/Hong Kong/97 (H5N1) viruses: J. of Infectious Diseases. 179:1132-1138.

Luytjes et al., 1989, "Amplification, Expression, and Packaging of a Foreign Gene by Influenza Virus", Cell 59:1107-1113.

Ma et al., "Identification of H2N3 influenza A viruses from swine in the United States," PNAS, 2007; 104(52):20949-20954.

Maassab et al., "Evaluation of a Cold-Recombinant Influenza Virus Vaccine in Ferrets", J. of Infectious Diseases, 146:780-790; (1982).

Maassab et al., "The Development of Live Attenuated Cold-adapted Influenza Virus Vaccine for Humans", Reviews in Medical Virology, 1999, vol. 9, pp. 237-245.

Maassab. "Adaptation and growth characteristics of influenza virus at 25 degrees C", Nature, 213:612-614 (1967).

Martin et al., 1998, "Studies of the Binding Properties of Influenza Hemagglutinin Receptor-Site Mutants", Virology 241:101-111.

Mena et al., 1994, "Synthesis of biologically active influenza virus core proteins using a vaccinia virus-T7 RNA polymerase expression system", J Gen Virol. 75:2109-14.

Mena et at, 1996, Rescue of a Synthetic Chloramphenicol Acetyltransferase RNA into Influenza Virus-Like Particles Obtained fro Recombinant Plasmids., J. Virol. 70: 5016-5024.

Merten et al., Production of influenza virus in Cell Cultures for Vaccine Preparation-, Novel Strategies in Design and Production of Vaccines, pp. 141-151; (1996).

Moyer et al., 1991, "Assembly and transcription of synthetic vesicular stomatitis virus nucleocapsids", J Virol. 65(5):2170-88.

Murphy & Coelingh, Principles Underlying the Development and Use of live Attenuated Cold-Adapted Influenza A and B Virus Vaccines, Viral Immunol. 15:295-323; (2002).

Muster et al., 1991, "An influenza A virus containing influenza B virus 5' and 3' noncoding regions on the neuraminidase gene .. :", Proc Natl Acad Sci USA 88:5177-81.

Naito and Ishihama, 1976, "Function and Structure of RNA Polymerase from Vesicular Stomatitis Virus", J. Biol. Chem. 251:4307-4314.

Nakajima et at, 2003, "Restriction of Amino Acid Change in Influenza A Virus H3HA: Comparison of Amino Acid Changes Observed .. ,", J. of Virology 77(18):10088-10098.

Nara et al.,1987, Simple, Rapid, Quantitative, Syncytium-Forming Micorassay for the Detection of Human Immunodeficiency . . . , AIDS Res. Hum. Retroviruses 3:283-302.

Nemeroff et al., 1998. "Influenza Virus NS1 Protein Interacts with the Cellular 30 kDa Subunit of CPSF and Inhibits 3'End Formation ..". Mol. Cell 1:991-1000.

Neumann et al., "Reverse Genetics for the Control of Avian Influenza", Avian Diseases, 2003, vol. 47, pp. 882-887.

(56) References Cited

OTHER PUBLICATIONS

Neumann et al., 1994, "RNA Polymerase I-Mediated Expression of Influenza Viral RNA Molecules", Virol. 202:477-479.
Neumann et al., 1999, "Generation of Influenza A viruses entirely from cloned cDNAs", PNAS 96(16):9345-9350.
Neumann, et al., Genetic Engineering of Influenza and Other Negative-Strand RNA Viruses Containing Segmented Genomes,—Advances in Virus Research, 1999; 53; 265-300.
Nichol et al. 1999, "Effectiveness of live. attenuated Intranasal influenza virus vaccine in healthy, working adults: a randomized controlled trial", JAMA 282:137-44.
Palese et aL. 1996, "Negative-Strand RNA Viruses: Genetic Engineering and Applications", Proc. Natl. Acad. Sci. USA 93.11354-11358.
Park et al., 1991, "Rescue of a Foreign Gene by Sendai Virus". Proc. Natl. Acad. Sci. USA 88:5537-5541.
Parkin et al., "Temperature Sensitive Mutants of Influenza A Virus Generated by Reverse Genetics . . . ". Virus Res., 46:31-44; (1996).
Parkin N. et al., Genetically Engineered live Attenuated Influenza A Virus Vaccine Candidates, J. Virol., pp. 2772-2778; (1997).
Partial European Search Report dated: Oct. 11, 2012 in European Application No. 12174997 filed on: May 20, 2005.
Pattnaik et al.. 1991. "Cells that express all five proteins of vesicular stomatitis virus from cloned cDNAs support replication .." Proc Natl Acad Sci USA 88:1379-83.
Peeters et al.. 1999. "Rescue of Newcastle Disease Virus from Cloned cDNA: Evidence that Cleavability of the Fusion Protein . . . ". J. Virol. 73:5001-5009.
Pekosz et al.. 1999. "Reverse genetics of negative-strand RNA viruses: closing the circle", Proc Natl Acad Sci USA. 96(16):8804-16.
Percy et al.. 1994. "Expression of a foreign protein by influenza A virus" J Virol 68(7):4486-92.
Perez, Daniel R. et al., 1998 "The Matrix 1 Protein of Influenza A Virus Inhibits the Transcriptase Activity of a Model . . . ", Article No. VY989318, Virology, 249:52-61.
Pleschka et al.. 1996. A Plasmid-Based Reverse Genetics System for I Influenza A Virus. J. Virol. 70:4188-4192.
Qiu et. al., 1994, "The influenza virus NS1 protein is a poly(A)-binding protein that inhibits nuclear export of mRNAs containing poly(A)", J Virol. 68(4):2425-32.
Qui et al., 1995. "The influenza virus NS1 protein binds to a specific region in human U6 snRNA and inhibits U6-U2 and U6-U4 snRNA..". RNA Society 1:304-16.
Racaniello et aJ., 1981. "Cloned Poliovirus Complementary DNA is Infectious in Mammalian Cells," Science 214:916-919.
Radecke et al., "Reverse Genetics Meets the Nonsegmented Negative-Strand RNA Viruses," Medical Virology, vol. 7: 49-63 (1997).
Radecke et al., 1995. "Rescue of measles viruses from cloned DNA". EMBO J. 14(23):5773-84.
Roberts and Rose. 1998, "Recovery of Negative-Strand RNA Viruses from Plasmid DNAs: a Positive Approach Revitalizes a Negative Field", Virol. 247:1-6.
Rose 1996. "Positive Strands to the Rescue Again: A Segmented Negative-Strand RNA Virus Derived from Cloned . . . ".PNAS USA 94:14998-15000.
Schickli et al., 2001, "Plasmid-only rescue of influenza A virus vaccine candidates", Philos Trans Society of London Ser B 356:1965-1973.
Schlesinger. 1995. "RNA viruses as vectors for the expression of heterologous proteins", Mol Biotechnol. 3:155-65.
Schnell et al.. 1994, "Infectious Rabies Viruses from Cloned cDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
See SCORE Sequence Results 1, 16.rup (2007).
See SCORE Sequence Results 1, 2, 15.rup (2007).
Seong et al., 1992, "A new method for reconstituting influenza polymerase and RNA in vitro: a study of the promoter elements for cRNA ..". Virology 186:247-60.
Sequence alignment of SEQ ID No. 6 in U.S. Appl. No. 12/699,108 UniProt database ID No: A9YN70_91 NFA of Ma et al. 2007.
Sequence alignment of SEQ ID No. 5 in U.S. Appl. No. 12/699,108 with SEQ ID No. 17 of US Patent No. 8,084,594 Gramer et al. Dec. 2007.
Shortridge et aL, 1998, "Characterization of H5N1 influenza viruse . . . " Virology 252(2):331-42.
Sidhu et at., 1995, "Rescue of synthetic measles virus minireplicons: measles genomic termini direct efficient expression . . . ", Virology. 208(2):800-07.
Snyder et al., "Four Viral Genes Independently Contribute to Attenuation of live Influenza A/Ann Arbor/6/60 (H2N2) Cold-Adapted . . . ", J. Virol., 62:488-95; (1988).
Suarez et al., "Comparisons of Highly Virulent H5NI Influenza A Viruses Isolated from Humans and Chickens from Hong Kong", Journal of Virology, vol. 72, No. 8 (1998), pp. 6678-6688.
Subbarao et al, 1995, "Sequential addition of temperature-sensitive missense mutations into the PB2 gene of influenza A . . . ", J. of Virology 69(10):5969-5917.
Subbarao et al., Evaluation of a genetically modified Reassortant H5N1 Influenza A Virus vaccine Candidate generated by plasmid-based Reverse genetics, 2003, Virology, vol. 305,, pp. 192-200.
Subbarao et al., The Attenuation Phenotype Conferred by the M Gene of the Influenza A/Ann Arbor/6/60 Cold-Adapted Virus (H2N2) on the . . . Virus Res., 25:37-50; (1992).
Suguitan et al., 2006, "Live, attenuated influenza A H5N1 candidate vaccines . . . " PLoS Med. Sep. 2006; 3(9):e360.
Szewczyk et al., 1988,"Purification, thioredoxin renaturation, and reconstituted activity of the three subunits of the influenza A virus RNA polymerase" Proc. Natl. Acad. Sci. USA 65:7907-7911.
Taylor et al., 1990, "Newcastle Disease Virus Fusion Protein Expressed in a Fowlpox Virus Recombinant Confers Protection in Chickens", J. Virol. 64:1441-1450.
Ward et al., 1988, "Direct Measurement of the Poliovirus RNA Polymerase Error Frequency in Vitro": J. Virol. 62:558-562.
Wareing et al., "Preparation and characterization of attenuated cold-adapted influenza A reassortants derived from the A/Leningrad/134/17/57 donor strain," Vaccine 2002;20:2082-2090.
Wareing et al., Vaccine 2005, vol. 23, Issue 31, pp. 4075-4081.
Wareing, J.M. et al., "Immunogenic and Isotope-Specific Responses to Russian and US Cold-Adapted Influenza A, Vaccine Donor . . . " J of Medical Virology (2001) 65:171-177.
Webby et al., 2004, "Responsiveness to a pandemic alert: use of reverse genetics for rapid development of influenza vaccines", Lancet 363: 1099-1103.
Weekly Epidemiological Record, "Outbreak News, Development of a Vaccine effective against avian influenza H5N1 Infection in Humans," Jan. 2004, vol. 79, No. 4, pp. 25-26.
Whelan et al., 1995, "Efficient recovery of infectious vesicular stomatitis virus entirely from cDNA clones", Proc.Natl.Acad.Sci. USA 92:8388-8392.
Xu et al., 1995 #AAB06964 (abstract only).
Xu et al., 1996, "Genetic Variation in Neuraminidase Genes of Influenza A (H3+A81N2) Viruses", Virology 224:175-183.
Xu, Xiyan, et al., 1999 n Genetic Characterization of the Pathogenic Influenza A/Goose/Guangdong/1/96 (H5N1) Virus: . . . Article 10 viro. 1999.9820. Virology 261:15-19.
Yamanaka et al.. 1991, "In vivo analysis of the promoter structure of the influenza virus RNA genome using a transfection system . . . ," Proc Natl Acad Sci USA 88: 5369-5373.
Yu et al., 1995, "Functional cDNA clones of the human respiratory syncytial (RS) virus N, P, and L proteins support replication . . . ", J Virol. 69(4):2412-19.
Yusoff et al., 1987, "Nucleotide Sequence Analysis of the L Gene of Newcastle Disease Virus: Homologies with Sendi and Vesicular Stomatitis.", Nucleic Acids Res. 15:3961-76.
Zaghouani et al., 1992, "Cells Expressing an H Chain' to Gene Carrying a Viral T Cell Epitope Are Lysed by Specific Cytolytic T Cells", J. Immunol. 148:3604-3609.

(56) References Cited

OTHER PUBLICATIONS

Zaghouani et al., 1991, "Induction of antibodies to the envelope protein of the human immunodeficiency virus by immunization . .", Proc. Natl. Acad Sci. USA 88:5645-5649.
Zhang and Air, 1994, "Expression of Functional Influenza Virus A Polymerase Proteins and Template from Cloned cDNAs ..", Biochem. & Biophys. Res. Commun. 200:95-101.
Zhang et al., "Persistence of four related human immunodeficiency virus subtypes during the course of zidovudine therapy: relationship between virion RNA and proviral DNA." J. Virol. 1994; 68(1): 425-432.
Zhou et al., "Rapid Evolution of H5N11 nfluenza Viruses in Chickens in Hong Kong," Journal of Virology, vol. 73, No. 4, pp. 3366-3374 (1999).
Zhou, et al., "Membrane-Anchored Incorporation of a Foreign Protein in Recombinant Influenza Virions", Article No. VY989169, Virology, 1998, vol. 246, pp. 83-94.
Zobel et al., 1993, "RNA polymerase I catalysed transcription of insert viral cDNA", Nucleic Acids Res. 21(16):3607-14.
Office Action mailed Dec. 8, 2008 in U.S. Appl. No. 11/133,360, filed May 20, 2005, published as: US/2005/0287172 on: Dec. 29, 2005 and issued as US. Pat. No. 7,527,800 on: May 5, 2009.
Office Action mailed Jun. 1, 2007 in U.S. Appl. No. 11/133,360, filed May 20, 2005, published as: US/2005/0287172 on: Dec. 29, 2005 and issued as US patent No. 7,527,800 on: May 5, 2009.
Office Action mailed Mar. 11, 2008 in U.S. Appl. No. 11/133,360, filed May 20, 2005, published as: US/2005/0287172 on: Dec. 29, 2005 and issued as US patent No. 7,527,800 on: May 5, 2009.
Office Action mailed on: Jan. 29, 2010 in U.S. Appl. No. 12/354,085 published as: 2009/0136530 on May 28, 2009 and Issued as U.S. Pat. No. 7,744,901 on Jun. 29, 2010.
Office Action mailed on: Jun. 18, 2009 in U.S. Appl. No. 12/354,085 , published as: 2009/0136530 on May 28, 2009 and Issued as U.S. Pat. No. 7,744,901 on Jun. 29, 2010.
Office Action mailed on: Dec. 28, 2012 in U.S. Appl. No. 13/230,203 published as: 2012/0009215 on Jan. 12, 2012.
Office Action mailed on: Sep. 27, 2012 in U.S. Appl. No. 13/230,203 published as: 2012/0009215 on Jan. 12, 2012.
Office Action mailed on: Mar. 14, 2012 in U.S. Appl. No. 13/230,203 published as: 2012/0009215 on Jan. 12, 2012.
Office Action mailed on: Oct. 1, 2010 in U.S. Appl. No. 11/836,413, published as: 2008/0069821 on Mar. 20, 2008.
Office Action mailed on: Jul. 8, 2013 in U.S. Appl. No. 13/077,488 published as: 2011/0182936 on Jul. 28, 2011.
Office Action mailed on: Oct. 16, 2012 in U.S. Appl. No. 13/077,488 published as: 2011/0182936 on Jul. 28, 2011.
Office Action mailed on: Mar. 27, 2012 in U.S. Appl. No. 13/077,488 published as: 2011/0182936 on Jul. 28, 2011.
Office Action mailed on: Sep. 10, 2010 in U.S. Appl. No. 11/836,369, published as: 2008/0057081 on Mar. 6, 2008.
Office Action mailed Sep. 6, 2006 in U.S. Appl. No. 11/133,360, filed May 20, 2005, published as: US/2005/0287172 on: Dec. 29, 2005 and issued as U.S. Pat. No. 7,527,800.
Office Action mailed on: Aug. 19, 2013 in U.S. Appl. No. 12/699,108, filed Feb. 3, 2010 and published as: 2010/0330118 on Dec. 30, 2010.
Office Action mailed on: Jan. 30, 2013 in U.S. Appl. No. 12/699,108, filed Feb. 3, 2010 and published as: 2010/0330118 on Dec. 30, 2010.
Office Action mailed: Mar. 10, 2011 in U.S. Appl. No. 12/399,312, filed Mar. 6, 2009 and published as: 2009/0175909 on: Jul. 9, 2009 and Issued as: U.S. Pat. No. 7,981,429 on Jul. 19, 2011.
Office Action mailed: Mar. 9, 2010 in U.S. Appl. No. 12/399,312, filed Mar. 6, 2009 and published as: 2009/0175909 on: Jul. 9, 2009 and Issued as: U.S. Pat. No. 7,981,429 on Jul. 19, 2011.
Office Action mailed: Nov. 26, 2010 in U.S. Appl. No. 12/399,312, filed Mar. 6, 2009 and published as: 2009/0175909 on: Jul. 9, 2009 and Issued as: U.S. Pat. No. 7,981,429 on Jul. 19, 2011.
Office Action mailed on: Sep. 27, 2013 in U.S. Appl. No. 12/769,304, filed Apr. 28, 2010 and published as: US-2011/0052618 on Mar. 3, 2011.
Office Action mailed on: Mar. 15, 2012 in U.S. Appl. No. 12/769,304, filed Apr. 28, 2010 and published as: US-2011/0052618 on Mar. 3, 2011.
Office Action mailed on: Jul. 12, 2011 in U.S. Appl. No. 12/769,304, filed Apr. 28, 2010 and published as: US-2011/0052618 on Mar. 3, 2011.
Office Action mailed on: Oct. 20, 2008 in U.S. Appl. No. 11/133,346, filed May 20, 2005, published as: US2006/0008473 on: Jan. 12, 2006 and issued as U.S. Pat. No. 7,504,109 on: Mar. 17, 2009.
Office Action mailed on: May 6, 2008 in U.S. Appl. No. 11/133,346, filed May 20, 2005, published as: US2006/0008473 on: Jan. 12, 2006 and issued as U.S. Pat. No. 7,504,109 on: Mar. 17, 2009
Office Action mailed on: Oct. 15, 2007 in U.S. Appl. No. 11/133,346, filed May 20, 2005, published as: US2006/0008473 on: Jan. 12, 2006 and issued as U.S. Pat. No. 7,504,109 on: Mar. 17, 2009.
Office Action mailed on: Apr. 20, 2007 in U.S. Appl. No. 11/133,346, filed May 20, 2005, published as: US2006/0008473 on: Jan. 12, 2006 and issued as U.S. Pat. No. 7,504,109 on: Mar. 17, 2009.
Office Action mailed: Jan. 27, 2012 in U.S. Appl. No. 13/161,938, filed Jun. 16, 2011 and published as: 2012/0034264 on: Feb. 9, 2012.
GenBank No. AAT69351.1 (published on Feb. 3, 2006), which discloses a neuraminidase sequence of A/GSC_chicken/British Columbia/04(H7N3).
Office Action mailed on Feb. 19, 2014 in U.S. Appl. No. 12/769,304, filed Apr. 28, 2010 and published as US 2011-0052618 on Mar. 3, 2011.
GenBank accession No. AAT78582.1, published: Dec. 14, 2014 hemagglutinin [Influenza A virus (A/chicken/British/Columbia/GSC_human_B/04(H7N3))].
GenBank Accession No. CAC84242.1, published Apr. 15, 2005, haemagglutinin,[Influenza A virus (A/duck/Hong Kong/221/77(H6N8))].
Office Action mailed on Jan. 22, 2015 in U.S. Appl. No. 13/784,259, filed Mar. 4, 2013 and published as US 2013-0189293 on Jul. 25, 2013.
Database EMBL [Online] E.B.I. Hinxton U.K., World Health Organization Global Influenza Program Surveillance: "Hemagglutinin," XP002684345, Database Accession No. Q4H2E2, Aug. 30, 2005.

* cited by examiner

INFLUENZA HEMAGGLUTININ AND NEURAMINIDASE VARIANTS

CROSS-REFERENCE TO RELATED APPLICATIONS

The present application is a divisional of U.S. patent application Ser. No. 12/699,108, filed Feb. 3, 2010, which claims the benefit of priority under 35 U.S.C. §119 to U.S. Provisional Application Ser. No. 61/152,094, filed Feb. 12, 2009, each of which are herein incorporated by reference in their entirety.

SEQUENCE LISTING

The instant application contains a Sequence Listing which has been submitted via EFS-Web and is hereby incorporated by reference in its entirety. The ASCII copy, created on Apr. 25, 2013, is named MDI-0439-UT.txt and is 27,154 bytes in size.

BACKGROUND OF THE INVENTION

Vaccines against various and evolving strains of influenza are important from a community health stand point, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread amongst various species, thereby necessitating the continuous production of new vaccines.

Numerous vaccines capable of producing a protective immune response specific for such different and influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application No. 60/420,708, filed Oct. 23, 2002; 60/574, 117, filed May 24, 2004; Ser. No. 10/423,828, filed Apr. 25, 2003; 60/578,962, filed Jun. 12, 2004; and Ser. No. 10/870, 690 filed Jun. 16, 2004, the disclosure of which is incorporated by reference herein.

Because of the continual emergence (or re-emergence) of different influenza strains, new influenza vaccines are continually desired. Such vaccines typically are created using antigenic moieties of the newly emergent virus strains, thus, polypeptides and polynucleotides of novel, newly emergent, or newly re-emergent virus strains (especially sequences of antigenic genes) are highly desirable.

The present invention provides new and/or newly isolated influenza hemagglutinin and neuraminidase variants that are capable of use in production of numerous types of vaccines as well as in research, diagnostics, etc. Numerous other benefits will become apparent upon review of the following.

SUMMARY OF THE INVENTION

In some aspects herein, the invention comprises an isolated or recombinant polypeptide that is selected from: a polypeptide comprising the amino acid sequence encoded by any one of SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5; a polypeptide comprising the amino acid sequence of any one of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6; a polypeptide comprising the amino acid sequence encoded by an open reading frame of any one of SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5; any alternative (e.g., the mature form without the signal peptide, or the polypeptide as present on the surface of a virus (e.g., influenza)) form of a polypeptide comprising the amino acid sequence of any one of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6; any polypeptide that is encoded by a polynucleotide which hybridizes under highly stringent conditions over substantially the entire length of a polynucleotide consisting of the nucleotide sequence selected from SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5; any polypeptide that is encoded by a polynucleotide which hybridizes under highly stringent conditions to a polynucleotide consisting of the nucleotide sequence selected from SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5; and, a fragment of any of the above wherein the sequence comprises a hemagglutinin or neuraminidase polypeptide, or a fragment of a hemagglutinin or neuraminidase polypeptide. In one embodiment, such polypeptide fragments generate an antibody that specifically binds a full length polypeptide of the invention. In various embodiments, the isolated or recombinant polypeptides of the invention are substantially identical to about 300 contiguous amino acid residues of any of the above polypeptides. In yet other embodiments, the invention comprises isolated or recombinant polypeptides, that comprise an amino acid sequence that is substantially identical over at least about 350 amino acids; over at least about 400 amino acids; over at least about 450 amino acids; over at least about 500 amino acids; over at least about 520 amino acids; over at least about 550 amino acids; over at least about 559 amino acids; over at least about 565 amino acids; or over at least about 566 amino acids contiguous of any of the above polypeptides. In some embodiments, the polypeptide sequence (e.g., as listed in "SEQUENCES" herein) comprises less than 565, 559, etc. amino acids. In such embodiments, the shorter listed polypeptides optionally comprise less than 565, 559, etc. amino acids. In yet other embodiments, the polypeptides of the invention (e.g., SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) optionally comprise fusion proteins, proteins with a leader sequence, a precursor polypeptide, proteins with a secretion signal or a localization signal, or proteins with an epitope tag, an E-tag, or a His epitope tag. In still other embodiments, the invention encompasses a polypeptide comprising an amino acid sequence having at least 85%, at least 90%, at least 93%, at least 95%, at least 98%, at least 98.5%, at least 99%, at least 99.2%, at least 99.4%, at least 99.6%, at least 99.8%, or at least 99.9% sequence identity to a polypeptide comprising the amino acid sequence selected from SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6. In another embodiment, a polypeptide of the invention comprises an amino acid sequence that differs from any one of SEQ ID NO: 2, 4, 6, 8, residues 16-340 of SEQ ID NO:2, residues 341-562 of SEQ ID NO:2, residues 16-340 of SEQ ID NO:6, or residues 341-562 of SEQ ID NO:6 at 1, 2, 3, 4, 5, 6, 7, 8, 9, 10, 15, 20, 25, 30, 35, 40, 45, or 50 amino acid residues. The hemagglutinin sequences of the invention can comprise both those sequences with unmodified and modified polybasic cleavage sites (thereby allowing growth of the viruses in eggs). The hemagglutinin polypeptide sequences of SEQ ID NOS:2 and 6 comprise the endogenous amino terminal signal peptide sequences, however, the hemagglutinin polypeptide sequences of the invention also include the mature (amino terminal signal peptide cleaved) form of the hemagglutinin polypeptides. The cleavage sites of any hemagglutinin polypeptide sequence of any influenza strain can be routinely measured or predicted using any number of methods in the art.

In other aspects, the invention comprises a composition with one or more polypeptide listed above, or fragments thereof. The invention also includes polypeptides that are specifically bound by a polyclonal antisera raised against at least 1 antigen that comprises at least one amino acid sequence described above, or a fragment thereof. Such antibodies specific for the polypeptides described above are also features of the invention. In one embodiment, the polypeptides of the invention are immunogenic.

The invention also encompasses immunogenic compositions comprising an immunologically effective amount of one or more of any of the polypeptides described above (e.g., SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) as well as methods for stimulating the immune system of an individual to produce a protective immune response against influenza virus by administering to the individual an immunologically effective amount of any of the above polypeptides in a physiologically acceptable carrier.

Additionally, the invention includes a reassortant influenza virus that comprises one or more of the polypeptides or polynucleotides above, in addition to immunogenic compositions comprising an immunologically effective amount of such reassortant influenza virus. Methods for stimulating the immune system of an individual to produce a protective immune response against influenza virus, through administering an immunologically effective amount of such reassortant influenza virus in a physiologically acceptable carrier are also part of the invention.

In other aspects, the invention comprises an isolated or recombinant polynucleotide that is selected from: a polynucleotide comprising any one of the nucleotide sequences of SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5 or complementary sequences thereof, a polynucleotide encoding a polypeptide comprising the amino acid sequence selected form SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6 or complementary nucleotide sequences thereof, a polynucleotide which hybridizes under highly stringent conditions over substantially the entire length of any of the above described polynucleotides, and a polynucleotide comprising all or a fragment of any of such nucleotide sequences wherein the sequence encodes a hemagglutinin or neuraminidase polypeptide or a fragment of a hemagglutinin or neuraminidase polypeptide. The invention also includes an isolated or recombinant polynucleotide that encodes an amino acid sequence which is substantially identical over at least about 300 amino acids of any polypeptide encoded by the above polynucleotides, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any polypeptide encoded by the above polynucleotides. Again, in situations wherein the amino acid is less than, e.g., 566, 565, 559, etc. in length (e.g., see, "SEQUENCES") then it should be understood that the length is optionally less than 566, 565, 559, etc. The invention also includes any of the above polynucleotides that comprise a nucleotide sequence encoding a hemagglutinin or neuraminidase polypeptide, or one or more fragments of one or more hemagglutinin or neuraminidase polypeptide. Other aspects of the invention include isolated or recombinant polynucleotides that encode a polypeptide (e.g., a hemagglutinin or neuraminidase polypeptide) whose sequence has at least 98% identity, at least 98.5% identity, at least 99% identity, at least 99.2% identity, at least 99.4% identity, at least 99.6% identity, at least 99.8% identity, or at least 99.9% identity to at least one of the above described polypeptides. The invention also includes isolated or recombinant polynucleotides encoding a polypeptide of hemagglutinin or neuraminidase produced by mutating or recombining one or more above described polynucleotides. In one embodiment, a polynucleotide of the invention may comprise a nucleotide sequence encoding one or more of, e.g., a leader sequence, a precursor sequence, or an epitope tag sequence or the like, and can optionally encode a fusion protein.

In yet other embodiments, the invention comprises a composition of matter having two or more above described polynucleotides (e.g., a library comprising at least about 2, 5, 10, 50 or more polynucleotides). Such compositions can optionally be produced by cleaving one or more above described polynucleotide (e.g., mechanically, chemically, enzymatically with a restriction endonuclease/RNAse/DNAse, etc.). Other compositions of the invention include, e.g., compositions produced by incubating one or more above described polynucleotide in the presence of deoxyribonucleotide triphosphates and a thermostable polynucleotide polymerase.

The invention also encompasses cells comprising at least one of the above described polynucleotides, or a cleaved or amplified fragment or product thereof. Such cells can optionally express a polypeptide encoded by such polynucleotide. Other embodiments of the invention include vectors (e.g., plasmids, cosmids, phage, viruses, virus fragments, etc.) comprising any of above described polynucleotides. Such vectors can optionally comprise an expression vector. Preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). Cells transduced by such vectors are also within the current invention.

In some embodiments, the invention encompasses a virus (e.g., an influenza virus) comprising one or more above described polynucleotides (e.g., encoding hemagglutinin and/or neuraminidase), or one or more fragments thereof. Immunogenic compositions comprising such virus are also part of the current invention. Such viruses can comprise a reassortant virus such as a 6:2 reassortant virus (e.g., comprising 6 internal genome segments from one or more donor virus and 2 genome segments (e.g., HA or NA genome segments) comprising one or more above described polynucleotide (or one or more fragment thereof). In one embodiment, the genome segment may encode a hemagglutinin and/or neuraminidase polypeptide of the invention. In one embodiment, a reassortant viruses of the invention is a live virus. In another embodiment, a reassortant virus of the invention is a temperature sensitive (ts), cold-adapted (ca), or attenuated (att) virus. In one embodiment, a reassortant virus of the invention comprises at least 1, at least 2, at least 3, at least 4, at least 5 or 6 internal genome segment of a donor virus (e.g., A/Ann Arbor/6/60, PR8, etc). In another embodiment, a reassortant virus of the invention comprises at least 1, at least 2, at least 3, at least 4, at least 5 or 6 internal genome segment of a donor virus other than A/Ann Arbor/6/60. One preferred embodiment of the invention is a reassortant influenza virus, wherein the virus is a 6:2 reassortant influenza virus and comprises 6 internal genome segments from A/Ann Arbor/6/60 and 2 genome segments that encode a polypeptide selected from the group consisting of: the polypeptides of SEQ ID NOS:2, 4, 6, 8, residues 16-340 of SEQ ID NO:2, residues 341-562 of SEQ ID NO:2, residues 16-340 of SEQ ID NO:6, and residues 341-562 of SEQ ID NO:6. In an alternative embodiment, a reassortant influenza virus of the invention includes a 6:2 reassortant influenza virus, wherein said virus comprises 6 internal genome segments from one or more donor viruses other than A/Ann Arbor/6/60 and 2 genome segments that encode a polypeptide selected from the group consisting of: the polypeptides of SEQ ID NOS:2, 4, 6, 8, residues 16-340 of SEQ ID NO:2, residues 341-562 of SEQ ID NO:2, residues 16-340 of SEQ ID NO:6, and residues 341-562 of SEQ ID NO:6. In another alternative embodiment, a reassortant influenza virus of the invention includes a 6:2 reassortant influenza virus, wherein said virus comprises 6 internal genome segments from one or more donor viruses other than A/Ann Arbor/6/60 and 2 genome segments, wherein the 2 genome segments encode HA and/or NA polypeptides from any pandemic influenza strain. Methods of producing a reassortant influenza virus through culturing a host cell harboring an influenza virus in a suitable culture medium under conditions permitting replication of the reassortant influenza virus and, isolating the reassortant influenza virus from one or more of the host cell or the medium are also part of the invention.

In other embodiments herein, the invention comprises immunogenic compositions having an immunologically effective amount of any of the above described reassortant influenza virus. Other embodiments include methods for stimulating the immune system of an individual to produce a protective immune response against influenza virus by administering to the individual an immunologically effective amount of any of the reassortant influenza virus described above (optionally in a physiologically effective carrier).

Other aspects of the invention include methods of producing an isolated or recombinant polypeptide by culturing any host cell above, in a suitable culture medium under conditions permitting expression of the polypeptide and, isolating the polypeptide from one or more of the host cells or the medium in which the cells are grown.

Immunogenic compositions are also features of the invention. For example, immunogenic compositions comprising one or more of any of the polypeptides and/or polynucleotides described above and, optionally, an excipient such as a pharmaceutically acceptable excipient or one or more pharmaceutically acceptable administration component. Immunogenic compositions of the invention can also comprise any one or more above described virus as well (e.g., along with one or more pharmaceutically acceptable administration component).

Methods of producing immunogenic responses in a subject through administration of an effective amount of any of the above viruses (or immunogenic compositions) to a subject are also within the current invention. Additionally, methods of prophylactic or therapeutic treatment of a viral infection (e.g., viral influenza) in a subject through administration of any one or more above described virus (or immunogenic compositions) in an amount effective to produce an immunogenic response against the viral infection are also part of the current invention. Subjects for such treatment include, but are not limited to, birds (e.g., poultry) and mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that are administered to the subject in an amount effect to prophylactically or therapeutically treat the viral infection.

In other aspects the invention includes compositions of matter comprising nucleotide sequences encoding hemagglutinin and/or neuraminidase polypeptides of one or more pandemic influenza strain and nucleotide sequences encoding one or more polypeptide of A/Ann Arbor/6/60. Additionally, the invention includes compositions of matter comprising nucleotide sequences encoding hemagglutinin and/or neuraminidase polypeptides of one or more pandemic influenza strain and nucleotide sequences encoding one or more polypeptide of PR8, A/Leningrad/17 or A/Ann Arbor/6/60. Such sequences can include those listed in the "SEQUENCES" herein. Additionally, preferred embodiments of the invention include compositions of matter comprising sequences encoding hemagglutinin and/or neuraminidase of one or more pandemic influenza strain and nucleotide sequences encoding a selected backbone strain in a 6:2 reassortant. Such compositions preferably include sequences encoding the hemagglutinin and neuraminidase selected from the "SEQUENCES" herein and a backbone strain, wherein the backbone strain is PR8, A/LENINGRAD/17 or A/Ann Arbor/6/60. The invention also includes such compositions as described above wherein the hemagglutinin comprises a modified polybasic cleavage site. The invention also includes live attenuated influenza vaccine comprising such above compositions.

These and other objects and features of the invention will become more fully apparent when the following detailed description is read in conjunction with the accompanying figures and appendix.

DETAILED DESCRIPTION

Figure 1:
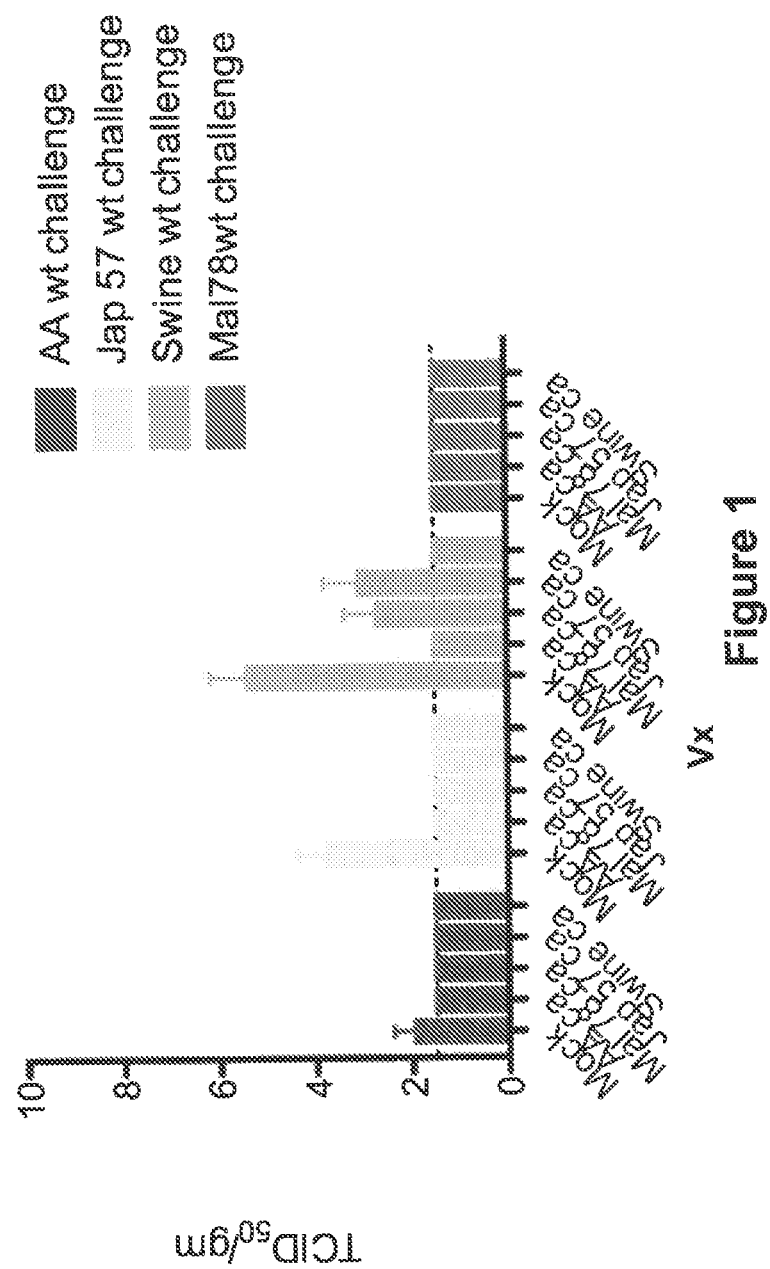
FIG. 1: Replication of H2 wt challenge viruses in lungs of ferrets vaccinated with various indicated H2 vaccine viruses. Titer represents average of right and left lungs.

The present invention includes influenza hemagglutinin and neuraminidase polypeptides and polynucleotides as well as vectors, compositions, reassortant influenza viruses and the like comprising such polypeptides and polynucleotides and methods of their use. Additional features of the invention are described in more detail herein.

Definitions

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a virus" includes a plurality of viruses; reference to a "host cell" includes mixtures of host cells, and the like.

The term "reassortant," when referring to a virus, indicates that the virus includes genetic and/or polypeptide components derived from more than one parental viral strain or source. For example, a 7:1 reassortant comprises 7 viral genome segments (or gene segments) from a first virus, and a single complementary viral genomic segment, e.g., encoding a hemagglutinin or neuraminidase of the invention. A 6:2 reassortant comprises 6 genome segments, e.g., the 6 internal genome segments from a first virus, and two complementary genome segments, i.e., hemagglutinin and neuraminidase encoding genome segments, from a second virus or a second and third virus.

The term "host cell" means a cell that contains a heterologous polynucleotide, such as a vector, and supports the replication and/or expression of the polynucleotide. Host cells can be prokaryotic cells such as E. coli, or eukaryotic cells such as yeast, insect, amphibian, avian or mammalian cells, including human cells. In one embodiment, host cells may be, but are not limited to, Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COST cells).

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with such influenza virus. In some instances, the influenza virus (e.g., naturally circulating) can still cause infection, but it cannot cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention, e.g., SEQ ID NO: 1-8, are variants of influenza HA and NA sequences. In general, influenza viruses are made up of an internal ribonucleoprotein core containing a segmented single-stranded RNA genome and an outer lipoprotein envelope lined by a matrix protein. The genome of influenza viruses is composed of eight genome segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); nonstructural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA).

Influenza is commonly grouped into influenza A and influenza B categories. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza Virus Vaccine

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (e.g., SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) are quite useful in constructing influenza vaccines. The current invention includes viruses/vaccines comprising HA and/or NA polypeptides and polynucleotides of A/Japan/57 and A/swine/MO/2006 (including wherein the HA polypeptides and polynucleotides comprise modified polybasic cleavage sites such as the modifications described herein); and including wherein the viruses/vaccines comprise a backbone (i.e. 6 internal genome segments) such as the backbone of ca A/AA/6/60, A/Leningrad/17 or PR8.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and/or NA sequences herein. See, Multi-Plasmid System for the production of Influenza virus, U.S. Application No. 60/420,708, filed Oct. 23, 2002, U.S. application Ser. No. 10/423,828, filed Apr. 25, 2003 and U.S. Application 60/574,117 filed May 24, 2004. Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and/or NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. In one embodiment, a master donor virus comprises 6 internal genome segments (i.e. a backbone) that confer one or more of the following properties: temperature sensitive, cold adapted, or attenuated. As explained elsewhere herein and, e.g., in U.S. patent application Ser. No. 10/423,828, etc., various embodiments of the invention utilize A/Ann Arbor (AA)/6/60 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortant with a number of other virus genes or virus types (e.g., a number of different "backbones" such as PR8, etc., containing the other influenza genes present in a reassortant, namely, the non-HA and non-NA genes.

Various embodiments herein can comprise live attenuated vaccines, having the HA and/or NA sequences herein, for A/Japan/57 or A/swine/MO/2006. Such vaccines typically comprise, e.g., the HA and/or NA polypeptides of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6, or their corresponding encoding nucleotides of SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5. One problem arising from growth of vaccine virus strains (e.g., reassortants) in eggs is that certain strains (which can be involved in pandemics) can kill the eggs in which the vaccines are to be produced and are, thus, hard to manipulate, produce, etc. through use of traditional (non-plasmid rescue) reassortant production. Such strains are of interest since evidence indicates they can result in influenza in humans and possible pandemics. Thus, use of plasmid-rescue systems to create/manipulate influenza reassortants with virus strains s (e.g., the HA and NA sequences herein) are quite desirable and are features of the invention. It will be appreciated, however, that the current sequences are also capable of use with non-plasmid or traditional systems.

In various embodiments herein, the antigenic sequences (e.g., the HA and/or NA polypeptides) as well as viruses and vaccines from such viruses comprise modified polybasic cleavage sites. Some highly pathogenic influenza strains comprise multiple basic amino acid cleavage sites within hemagglutinin sequences. See, e.g., Li et al., *J. of Infectious Diseases*, 179:1132-8, 1999. Such cleavage sites, in typical embodiments herein, are, e.g., modified or altered in their sequences in comparison to the wild-type sequences from which the current sequences are derived (e.g., to disable the cleavage or reduce the cleavage there, etc.). Such modifications/alterations can be different in different strains due to the various sequences of the cleavage sites in the wild-type sequences. For example, 4 polybasic residues (arginine-arginine-lysine-lysine (SEQ ID NO: 9)) at 326-329 of mature H5 are typically removed in sequences herein (as compared to wt). In various embodiments, the polybasic cleavage sites can be modified in a number of ways (all of which are contained within the invention). For example, the polybasic cleavage site can be removed one amino acid at a time (e.g., one arginine removed, two arginines removed, two arginines and lysine removed, or two arginines and two lysines removed). Additionally, the amino acid residue directly upstream of the cleavage site can also be removed or altered (e.g., from an R to a T, etc.); also, the nucleotides encoding the amino acid residue directly after the cleavage site can also be modified. In addition, hemagglutinin polypeptide sequences of influenza virus comprise amino terminal signal peptide sequences, thus, the hemagglutinin polypeptide sequences of the invention include both the mature (amino terminal signal peptide cleaved) form of the hemagglutinin polypeptides and the pre-cleaved form of hemagglutinin. The cleavage sites of any hemagglutinin polypeptide sequence of any influenza strain can be routinely measured or predicted using any number of methods in the art.

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Again, the HA and NA sequences of the current invention are optionally utilized in the production of or in reassortant vaccines (and/or in other ts, cs, ca, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., any of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6, or the corresponding nucleotides encoding the specific HA and NA antigens, e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5).

FluMist™

As mentioned previously, numerous examples and types of influenza vaccine exist. An example of an influenza vaccine is FluMist™ which is a live, attenuated vaccine that protects children and adults from influenza illness (Belshe et al. (1998) *The efficacy of live attenuated, cold-adapted, trivalent, intranasal influenza virus vaccine in children N Engl J Med* 338:1405-12; Nichol et al. (1999) *Effectiveness of live, attenuated intranasal influenza virus vaccine in healthy, working adults: a randomized controlled trial JAMA* 282:137-44). The methods and compositions of the current invention may be adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the strains (e.g., wild-type strains) to which the vaccine is addressed along with six gene segments, PB1, PB2, PA, NP, M and NS, from a common master donor virus (MDV). The HA sequences herein, thus, may be part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C. Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N Engl J Med* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J Infect Dis* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900).

Production of such reassorted virus using B strains of influenza is more difficult, however, recent work (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004) has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences (e.g., nucleotide sequences SEQ ID NO: 1, 3, 5, 7, residues 89-1063 of SEQ ID NO:1, residues 1064-1729 of SEQ ID NO:1, residues 88-1062 of SEQ ID NO:5 or residues 1063-1728 of SEQ ID NO:5 and the corresponding amino acids encoded by the nucleotide sequences in SEQ ID NO: 2, 4, 6, 8, residues 16-340 of SEQ ID NO:2, residues 341-562 of SEQ ID NO:2, residues 16-340 of SEQ ID NO:6, or residues 341-562 of SEQ ID NO:6), methods, etc. of the current invention, are optionally used in conjunction with, or in combination with, such previous work involving, e.g., reassorted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO: 1, 3, 5, 7, residues 89-1063 of SEQ ID NO:1, residues 1064-1729 of SEQ ID NO:1, residues 88-1062 of SEQ ID NO:5 or residues 1063-1728 of SEQ ID NO:5 or polypeptides of SEQ ID NO: 2, 4, 6, 8, residues 16-340 of SEQ ID NO:2, residues 341-562 of SEQ ID NO:2, residues 16-340 of SEQ ID NO:6, or residues 341-562 of SEQ ID NO:6, or fragments thereof) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., comprising an HA and/or NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., *Infect. Immun.* 37:397-400 (1982); Kim et al., *Pediatrics* 52:56-63 (1973); and Wright et al., *J. Pediatr.* 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response may be elicited with a single dose, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention, e.g., any of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) or an expression vector comprising a polynucleotide (e.g., any of SEQ ID NO: 1, 3, 5, 7, residues 89-1063 of SEQ ID NO:1, residues 1064-1729 of SEQ ID NO:1, residues 88-1062 of SEQ ID NO:5 or residues 1063-1728 of SEQ ID NO:5) encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two strains, e.g., each of which represents a different subgroup. Additionally, vaccine combinations can optionally include mixes of pandemic vaccines (e.g., those against pandemic influenza strains such as various avian strains, see, e.g., the sequences herein, or other pandemic strains) and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents.

Polynucleotides of the Invention

It is well known in the art that the HA and NA polynucleotide segments of influenza viruses comprise both a coding region (encoding the ORF) and noncoding regions (NCRs), both 5' and 3' of the HA and NA coding sequence. It is also known that primers can be made to these NCRs to facilitate amplification of the entire HA and NA segments of influenza virus. (see, e.g., Hoffmann et al. Arch Virol. 2001 December; 146(12):2275-89). Further, it is known that the NCRs of the HA and NA of influenza may increase the efficiency of achieving reassortants. Therefore, the nucleotide sequences of these NCRs (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9% identity) thereof) are within the scope of this invention. When amplifying the HA and NA segments of any pandemic strain, one could make and use polynucleotide primers to bind conserved (e.g., among related strains) regions of the HA and NA NCRs for amplification (e.g., by RT-PCR). In one embodiment, HA and NA polynucleotides of the invention include both the NCR and ORF of the HA and NA sequences (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9%) thereof) of pandemic virus strains. In alternative embodiments, the HA and NA polynucleotides of the invention exclude the NCR, but include the ORF (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9% thereof)) of the HA and NA sequences of pandemic virus strains (e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5).

The HA and NA polynucleotides of the invention, e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5, and fragments thereof, are optionally used in a number of different capacities alternative to, or in addition to, the vaccines described above. Other exemplary uses are described herein for illustrative purpose and not as limitations on the actual range of uses. Different methods of construction, purification, and characterization of the nucleotide sequences of the invention are also described herein. In some embodiments, polynucleotides including one or more nucleotide sequence of the invention are favorably used as probes for the detection of corresponding or related polynucleotides in a variety of contexts, such as in nucleic hybridization experiments, e.g., to find and/or characterize homologous influenza variants (e.g., homologues to the sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a nucleotide sequence or subsequence selected, e.g., from among SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5, or sequences complementary thereto. Alternatively, nucleotide sequences that are variants of one of the above-designated sequences are used as probes. Most typically, such variants include one or a few conservative nucleotide variations. For example, pairs (or sets) of oligonucleotides can be selected, in which the two (or more) nucleotide sequences are conservative variations of each other, wherein one nucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of the sequences herein, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite triester method described by Beaucage and Caruthers (1981) *Tetrahedron Letts* 22(20):1859-1862, e.g., using an automated synthesizer, or as described in Needham-Van Devanter et al. (1984) *Nucl Acids Res*, 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J Chrom* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention (e.g., SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) and/or encoded by polynucleotide sequences of the invention, e.g., selected from SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5 are favorably used to identify and isolate antibodies, e.g., from phage display libraries, combinatorial libraries, polyclonal sera, and the like. Polypeptide fragments of the inventions include a peptide or polypeptide comprising an amino acid sequence of at least 5 contiguous amino acid residues, or at least 10 contiguous amino acid residues, or at least 15 contiguous amino acid residues, or at least 20 contiguous amino acid residues, or at least 25 contiguous amino acid residues, or at least 40 contiguous amino acid residues, or at least 50 contiguous amino acid residues, or at least 60 contiguous amino residues, or at least 70 contiguous amino acid residues, or at least contiguous 80 amino acid residues, or at least contiguous 90 amino acid residues, or at least contiguous 100 amino acid residues, or at least contiguous 125 amino acid residues, or at least 150 contiguous amino acid residues, or at least contiguous 175 amino acid residues, or at least contiguous 200 amino acid residues, or at least contiguous 250 amino acid residues, or at least contiguous 350, or at least contiguous 400, or at least contiguous 450, or at least contiguous 500, or at least contiguous 550 amino acid residues of the amino acid sequence an HA or NA polypeptide of the invention (e.g., SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6). Polynucleotides encoding said polypeptide fragments and antibodies that specifically bind said polypeptides are also preferred embodiments of the invention.

Antibodies specific for any polypeptide sequence or subsequence, e.g., of SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6, and/or encoded by polynucleotide sequences of the invention, e.g., selected from SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5 are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Additional details regarding production of specific antibodies are provided below.

Diagnostic Assays

The polynucleotide sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify polynucleotides using polymerase chain reaction (PCR) methods well known in the art (e.g., reverse transcription-PCR) and as probes in polynucleotide hybridization assays to detect target genetic material such as influenza RNA in clinical specimens.

The probes of the invention, e.g., as exemplified by unique subsequences selected from those given herein, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral polynucleotides (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza polynucleotides in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to polynucleotides originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the polynucleotide sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5 or a subsequence thereof etc., has been inserted, in a forward or reverse orientation. For example, the inserted polynucleotide can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or fragments thereof). Such vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate polynucleotide sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortant. See, e.g., U.S. Application No. 60/420,708, filed Oct. 23, 2002; 60/574,117, filed May 24, 2004; Ser. No. 10/423,828, filed Apr. 25, 2003; 60/578,962, filed Jun. 12, 2004; and Ser. No. 10/870,690 filed Jun. 16, 2004; and US20020164770, which are incorporated by reference herein. For example, preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). The reassortants produced can include the HA and NA genes arranged with the 6 other influenza genes from the A/Ann Arbor/6/60 donor strain (and/ or derivatives and modifications thereof), the PR8 donor strain backbone, the A/Leningrad/17 donor strain backbone, etc. Other backbone strains are described, for example, in 20040137013 and 20030147916, which are incorporated by reference herein.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a polynucleotide sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) *Results Probl Cell Differ* 20:125-62; Bittner et al. (1987) *Methods in Enzymol* 153:516-544).

Production of Recombinant Virus

Negative strand RNA viruses can be genetically engineered and recovered using a recombinant reverse genetics approach (see, e.g., U.S. Pat. No. 5,166,057 to Palese et al.). Such method was originally applied to engineer influenza viral genomes (Luytjes et al. (1989) Cell 59:1107-1113; Enami et al. (1990) *Proc. Natl. Acad. Sci. USA* 92:11563-11567), and has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al. (1995) *EMBO J.* 14:5773-5784); rinderpest virus (Baron & Barrett (1997) *J. Virol.* 71: 1265-1271); human parainfluenza virus (Hoffman & Banerjee (1997) *J. Virol.* 71: 3272-3277; Dubin et al. (1997) *Virology* 235:323-332); SV5 (He et al. (1997) *Virology* 237:249-260); canine distemper virus (Gassen et al. (2000) *J. Virol.* 74:10737-44); and Sendai virus (Park et al. (1991) *Proc. Natl. Acad. Sci. USA* 88: 5537-5541; Kato et al. (1996) Genes to Cells 1:569-579). Those of skill in the art will be familiar with these and similar techniques to produce influenza virus comprising the HA and NA sequences of the invention. Reassortant influenza viruses produced according to such methods are also a feature of the invention, as are reassortant influenza virus comprising one or more polynucleotides and/or polypeptides of the invention.

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda.*

Most commonly, mammalian cells are used to culture the HA and NA molecules of the invention. Suitable host cells for the replication of influenza virus include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences. The culture conditions, such as temperature, pH and the like, are typically those previously used with the particular host cell selected for expression, and will be apparent to those skilled in the art and in the references cited herein, including, e.g., Freshney (1994) *Culture of Animal Cells, a Manual of Basic Technique,* 3$^{rd}$ edition, Wiley-Liss, New York and the references cited therein. Other helpful references include, e.g., Paul (1975) *Cell and Tissue Culture,* 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*, in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous polynucleotides into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 μg of each vector is introduced into a population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5\times10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) *Proc Natl Acad Sci* 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the polynucleotides of the invention can also be produced in non-animal cells such as plants, yeast, fungi, bacteria and the like. In addition to Sambrook, Berger and Ausubel, all infra, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); *Methods in Enzymology* 153: 516-544.

Nucleic Acid Hybridization

Comparative hybridization can be used to identify nucleic acids (e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5) of the invention, including conservative variations of nucleic acids of the invention. This comparative hybridization method is a preferred method of distinguishing nucleic acids of the invention. In addition, target nucleic acids which hybridize to the nucleic acids represented by, e.g., those shown herein under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe and target under conditions in which a perfectly matched probe binds to a perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, Sambrook, and Berger and Kimmel, all below. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer and other nucleic acid hybridization parameters). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of a probe to a perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein (e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5) and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention, e.g., SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5).

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid is said to bind to the probe under ultra-ultra-high stringency conditions and are also features of the invention.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules as in SEQ ID NO: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., *Nature Biotechnology*, 19:456-460 (2001); Ling et al., *Approaches to DNA mutagenesis: an overview*, Anal Biochem 254(2): 157-178 (1997); Dale et al., *Oligonucleotide-directed random mutagenesis using the phosphorothioate method*, Methods Mol Biol 57:369-374 (1996); I. A. Lorimer, I. Pastan, *Nucleic Acids Res* 23, 3067-8 (1995); W. P. C. Stemmer, *Nature* 370, 389-91 (1994); Arnold, *Protein engineering for unusual environments*, Current Opinion in Biotechnology 4:450-455 (1993); Bass et al., *Mutant Trp repressors with new DNA-binding specificities*, Science 242:240-245 (1988); Fritz et al., *Oligonucleotide-directed construction of mutations: a gapped duplex DNA procedure without enzymatic reactions in vitro*, Nucl Acids Res 16: 6987-6999 (1988); Kramer et al., *Improved enzymatic in vitro reactions in the gapped duplex DNA approach to oligonucleotide-directed construction of mutations*, Nucl Acids Res 16: 7207 (1988); Sakamar and Khorana, *Total synthesis and expression of a gene for the α-subunit of bovine rod outer segment guanine nucleotide-binding protein (transducin)*, Nucl Acids Res 14: 6361-6372 (1988); Sayers et al., *Y-T Exonucleases in phosphorothioate-based oligonucleotide-directed mutagenesis*, Nucl Acids Res 16:791-802 (1988); Sayers et al., *Strand specific cleavage of phosphorothioate-containing DNA by reaction with restriction endonucleases in the presence of ethidium bromide*, (1988) Nucl Acids Res 16: 803-814; Carter, *Improved oligonucleotide-directed mutagenesis using M13 vectors*, Methods in Enzymol 154: 382-403 (1987); Kramer & Fritz *Oligonucleotide-directed construction of mutations via gapped duplex DNA*, Methods in Enzymol 154:350-367 (1987); Kunkel, *The efficiency of oligonucleotide directed mutagenesis, in Nucleic Acids & Molecular Biology* (Eckstein, F. and Lilley, D. M. J. eds., Springer Verlag, Berlin)) (1987); Kunkel et al., *Rapid and efficient site-specific mutagenesis without phenotypic selection*, Methods in Enzymol 154, 367-382 (1987); Zoller & Smith, *Oligonucleotide-directed mutagenesis: a simple method using two oligonucleotide primers and a single-stranded DNA template*, Methods in Enzymol 154: 329-350 (1987); Carter, *Site-directed mutagenesis*, Biochem J 237:1-7 (1986); Eghtedarzadeh & Henikoff, *Use of oligonucleotides to generate large deletions*, Nucl Acids Res 14: 5115 (1986); Mandecki, *Oligonucleotide-directed double-strand break repair in plasmids of Escherichia coli: a method for site-specific mutagenesis*, Proc Natl Acad Sci USA, 83:7177-7181 (1986); Nakamaye & Eckstein, *Inhibition of restriction endonuclease Nci I cleavage by phosphorothioate groups and its application to oligonucleotide-directed mutagenesis*, Nucl Acids Res 14: 9679-9698 (1986); Wells et al., *Importance of hydrogen-bond formation in stabilizing the transition state of subtilisin*, Phil Trans R Soc Lond A 317: 415-423 (1986); Botstein & Shortle, *Strategies and applications of in vitro mutagenesis*, Science 229:1193-1201 (1985); Carter et al., *Improved oligonucleotide site-directed mutagenesis using M13 vectors*, Nucl Acids Res 13: 4431-4443 (1985); Grundström et al., *Oligonucleotide-directed mutagenesis by microscale 'shot-gun' gene synthesis*, Nucl Acids Res 13: 3305-3316 (1985); Kunkel, *Rapid and efficient site-specific mutagenesis without phenotypic selection*, Proc Natl Acad Sci USA 82:488-492 (1985); Smith, *In vitro mutagenesis*, Ann Rev Genet. 19:423-462 (1985); Taylor et al., *The use of phosphorothioate-modified DNA in restriction enzyme reactions to prepare nicked DNA*, Nucl Acids Res 13: 8749-8764 (1985); Taylor et al., *The rapid generation of oligonucleotide-directed mutations at high frequency using phosphorothioate-modified DNA*, Nucl Acids Res 13: 8765-8787 (1985); Wells et al., *Cassette mutagenesis: an efficient method for generation of multiple mutations at defined sites*, Gene 34:315-323 (1985); Kramer et al., *The gapped duplex DNA approach to oligonucleotide-directed mutation construction*, Nucl Acids Res 12: 9441-9456 (1984); Kramer et al., *Point Mismatch Repair*, Cell 38:879-887 (1984); Nambiar et al., *Total synthesis and cloning of a gene coding for the ribonuclease S protein*, Science 223: 1299-1301 (1984); Zoller & Smith, *Oligonucleotide-directed mutagenesis of DNA fragments cloned into M13 vectors, Methods in Enzymol* 100: 468-500 (1983); and Zoller & Smith, *Oligonucleotide-directed mutagenesis using M13-derived vectors: an efficient and general procedure for the production of point mutations in any DNA fragment, Nucl Acids Res* 10:6487-6500 (1982). Additional details on many of the above methods can be found in *Methods in Enzymol* Volume 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, *Tetrahedron Letts* 22(20):1859-1862, (1981) e.g., using an automated synthesizer, as described in Needham-VanDevanter et al., *Nucleic Acids Res,* 12:6159-6168 (1984).

In addition, essentially any polynucleotide can be custom or standard ordered from any of a variety of commercial sources, such as The Midland Certified Reagent Company (mcrc@oligos(dot)com), The Great American Gene Company (www(dot)genco(dot)com), ExpressGen Inc. (www(dot)expressgen(dot)com), Operon Technologies Inc. (Alameda, Calif.) and many others. Similarly, peptides and antibodies can be custom ordered from any of a variety of sources, such as PeptidoGenic (available at pkim@ccnet(dot)com), HTI Bio-products, Inc. (www(dot)htibio(dot)com), BMA Biomedicals Ltd. (U.K.), Bio.Synthesis, Inc., and many others.

The present invention also relates to host cells and organisms comprising a HA and/or NA molecule or other polypeptide and/or polynucleotide of the invention, e.g., SEQ ID NOS: SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., *Proc Natl Acad Sci USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optionally both. See, Giliman & Smith, *Gene* 8:81 (1979); Roberts, et al., *Nature,* 328:731 (1987); Schneider, B., et al., *Protein Expr Purif* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY. See, above. Further vectors useful with the sequences herein are illustrated above in the section concerning production of influenza virus for vaccines and the references cited therein.

Polypeptide Production and Recovery

Following transduction of a suitable host cell line or strain and growth of the host cells to an appropriate cell density, the selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing a HA and/or a NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules (or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) *Bioseparation of Proteins,* Academic Press, Inc.; and Bollag et al. (1996) *Protein Methods, $2^{nd}$ Edition* Wiley-Liss, NY; Walker (1996) *The Protein Protocols Handbook*

Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3$^{rd}$ Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds.) *Textbook of Influenza pp.* 324-332; Merten et al. (1996) *Production of influenza virus in cell cultures for vaccine preparation*, in Cohen & Shafferman (eds.) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer.

Alternatively, cell-free transcription/translation systems can be employed to produce polypeptides comprising an amino acid sequence or subsequence of, e.g., the sequences given herein such as SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6, or encoded by the polynucleotide sequences of the invention, e.g., SEQ ID NOS: SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) *Solid-Phase Peptide Synthesis*, WH Freeman Co, San Francisco; Merrifield J (1963) *J Am Chem Soc* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc Amino acid(s) are modified, for example, co-translationally or post-translationally during recombinant production (e.g., N-linked glycosylation at N-X-S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Fusion Proteins

The present invention also provides fusion proteins comprising fusions of the sequences of the invention (e.g., encoding HA and/or NA polypeptides as exampled by SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of target polypeptides.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) *Current Protocols in Immunology* Wiley/Greene, NY; Paul (ed.) (1998) *Fundamental Immunology, Fourth Edition*, Lippincott-Raven, Lippincott Williams & Wilkins; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) Science 246: 1275-1281; and Ward, et al. (1989) Nature 341: 544-546. Specific monoclonal and polyclonal antibodies and antisera will usually bind with a $K_D$ of, e.g., at least about 0.1 µM, at least about 0.01 µM or better, and, typically and at least about 0.001 µM or better.

For certain therapeutic applications, humanized antibodies are desirable. Detailed methods for preparation of chimeric (humanized) antibodies can be found in U.S. Pat. No. 5,482,856. Additional details on humanization and other antibody production and engineering techniques can be found in Borrebaeck (ed.) (1995) *Antibody Engineering, 2$^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983), *Hybridoma* 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein (e.g., SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6), etc. To eliminate cross-reactivity with other homologues, the antibody or antisera is subtracted with the HA and/or NA molecules found in public databases at the time of filing, e.g., the "control" polypeptide(s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein (e.g., SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6), etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about a ½ signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide(s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein (e.g., SEQ ID NOS: 1-8). However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

Conservative Substitution Groups

| | | | |
|---|---|---|---|
| 1 Alanine (A) | Serine (S) | Threonine (T) | |
| 2 Aspartic acid (D) | Glutamic acid (E) | | |
| 3 Asparagine (N) | Glutamine (Q) | | |
| 4 Arginine (R) | Lysine (K) | | |
| 5 Isoleucine (I) | Leucine (L) | Methionine (M) | Valine (V) |
| 6 Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein, e.g., SEQ ID NOS: SEQ ID NO:1, 3, 5, 7, residues 89-1063 of SEQ ID NO:1, residues 1064-1729 of SEQ ID NO:1, residues 88-1062 of SEQ ID NO:5 and residues 1063-1728 of SEQ ID NO:5. The unique subsequence is unique as compared to a nucleic acids corresponding to nucleic acids such as, e.g., those found in GenBank or other similar public databases at the time of filing. Alignment can be performed using, e.g., BLAST set to default parameters. Any unique subsequence is useful, e.g., as a probe to identify the nucleic acids of the invention. See, above.

Similarly, the invention includes a polypeptide which comprises a unique subsequence in a polypeptide selected from the sequence of HA and NA molecules disclosed herein, e.g., SEQ ID NOS: 2, 4, 6, 8, residues 16-340 of SEQ ID NO:2, residues 341-562 of SEQ ID NO:2, residues 16-340 of SEQ ID NO:6, and residues 341-562 of SEQ ID NO:6. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, at least about 250 residues, at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol Biol* 48:443 (1970), by the search for similarity method of Pearson & Lipman, *Proc Natl Acad Sci USA* 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., *J Mol Biol* 215:403-410 (1990). Software for performing BLAST analyses is publicly available through the National Center for Biotechnology Information (www(dot)ncbi.nlm.nih(dot)gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc Natl Acad Sci USA* 89:10915).

In addition to calculating percent sequence identity, the BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) CABIOS 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit can also further comprise, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like.

To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

EXAMPLES

H2N2 influenza viruses caused the 1957 pandemic and circulated in humans until 1968 when they were replaced by H3N2 influenza viruses. Having proven capable of causing disease, H2 viruses may have pandemic potential given the lack of H2 specific immunity in persons born after 1968. Fourteen geographically and temporally diverse H2 avian and human influenza viruses were evaluated for their ability to replicate and elicit a broad cross reactive antibody response in ferrets. Sera from ferrets that were inoculated with influenza A/Japan/57 (H2N2), A/mallard/NY/78 (H2N2) and A/swine/ MO/2006 (H2N3) viruses elicited a broadly cross-reactive antibody response against heterologous H2 viruses in hemagglutination-inhibition and neutralization assays.

Using an A/Ann Arbor/6/60 (AA) cold-adapted (ca) (H2N2) backbone, three ca viruses were generated: ca A/Japan/57, ca A/mallard/NY/78 and ca A/swine/MO/2006. The HA and NA sequences of A/Japan/57 and A/swine/MO/2006 are shown in Table 3. The ability of each ca vaccine virus to protect against homologous and heterologous wild type (wt) H2 virus challenge was evaluated in ferrets. Efficacy of protection was variable in the upper respiratory tract. The ca AA and ca A/Japan/57 vaccines provided complete protection against a homologous challenge while the ca A/mallard/NY/ 78 and ca A/swine/MO/2006 vaccines provided partial protection from homologous challenge with a significant reduction in virus titers compared with mock-immunized animals. None of the ca vaccine viruses conferred complete protection against heterologous challenge in the upper respiratory tract. In the lower respiratory tract, each ca vaccine conferred complete protection from the challenge with the homologous wt virus. The ca AA and ca A/swine/MO/2006 vaccines provided complete protection in the lower respiratory tract against all heterologous wt challenge viruses.

TABLE 3

HA/NA sequences of the reassortant vaccine strains.

| SEQ ID NO | HA or NA | Strain Name | Amino Acid or Nucleotide |
|---|---|---|---|
| SEQ ID NO: 1 | HA (H3) | ca A/Japan/57 | Nucleotide |
| SEQ ID NO: 2 | HA (H3) | ca A/Japan/57 | Amino Acid |
| SEQ ID NO: 3 | NA (N2) | ca A/Japan/57 | Nucleotide |
| SEQ ID NO: 4 | NA (N2) | ca A/Japan/57 | Amino Acid |
| SEQ ID NO: 5 | HA (H3) | ca A/swine/MO/2006 | Nucleotide |
| SEQ ID NO: 6 | HA (H3) | ca A/swine/MO/2006 | Amino Acid |
| SEQ ID NO: 7 | NA (N3) | ca A/swine/MO/2006 | Nucleotide |
| SEQ ID NO: 8 | NA (N3) | ca A/swine/MO/2006 | Amino Acid |

Figure 2:
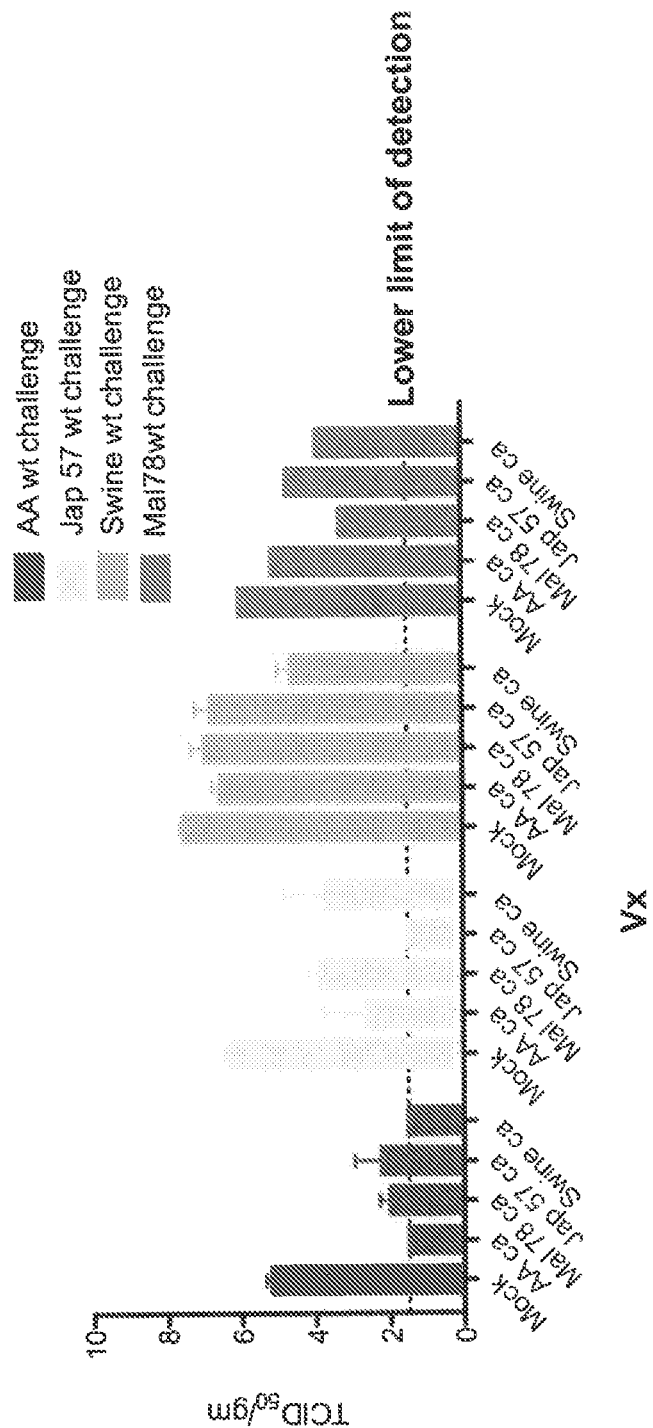
FIG. 2: Replication of H2 wt challenge viruses in NT of ferrets vaccinated with various indicated H2 vaccine viruses.

FIGS. 1 and 2 show the efficacy of protection conferred by the ca AA, ca A/Japan/57, ca A/mallard/NY/78 and ca A/swine/MO/2006 vaccines in ferrets. Ferrets were vaccinated with a single dose of ca reassortant virus vaccine. The ferrets were then challenged with wt AA, wt A/Japan/57, wt A/mallard/NY/78 and wt A/swine/MO/2006 influenza virus. Three days post challenge lungs and nasal turbinates of the ferrets were harvested and virus titer in the tissues was determined FIGS. 1 and 2 shows efficacy of protection conferred by the recombinant H2 vaccines against homologous and heterologous wild-type H2 viruses in lungs and nasal turbinates, respectively, in ferrets.

Figure 3:
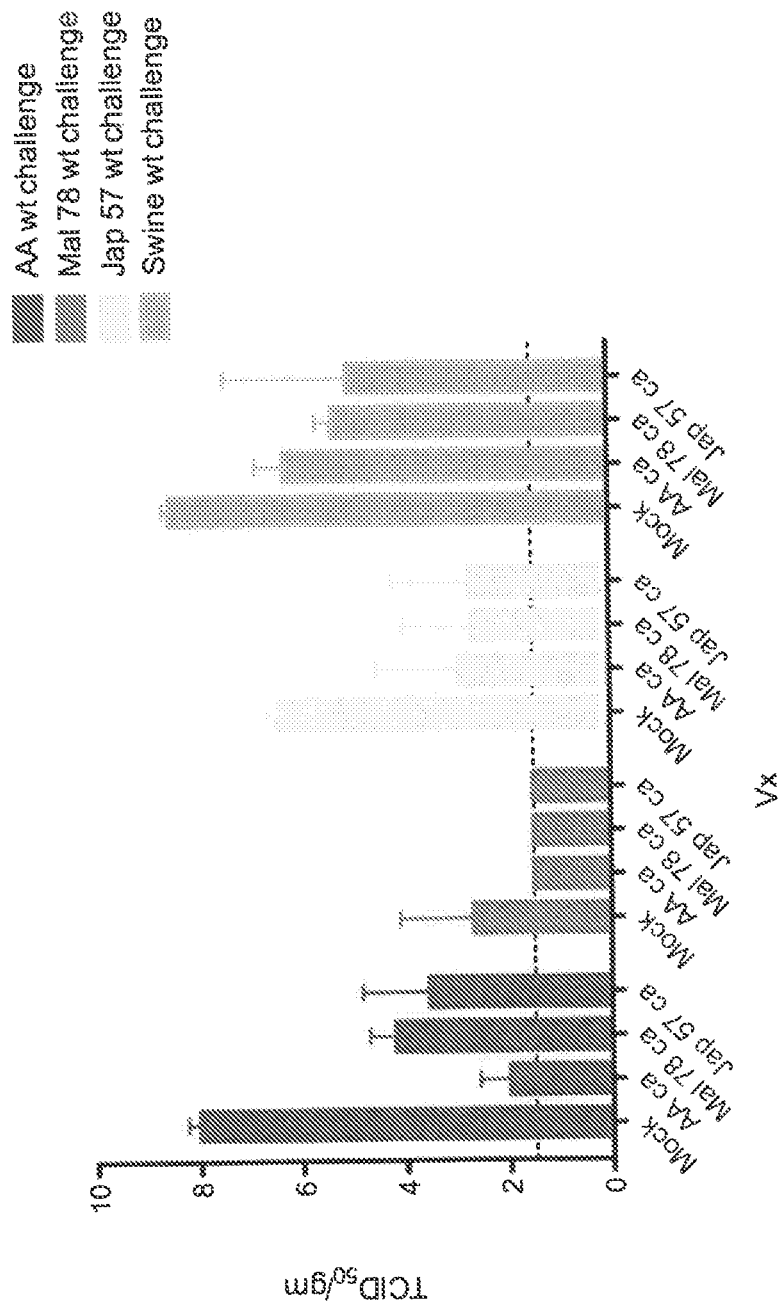
FIG. 3: Replication of H2 wt challenge viruses in lungs of mice vaccinated with various indicated H2 vaccine viruses.
Figure 4:
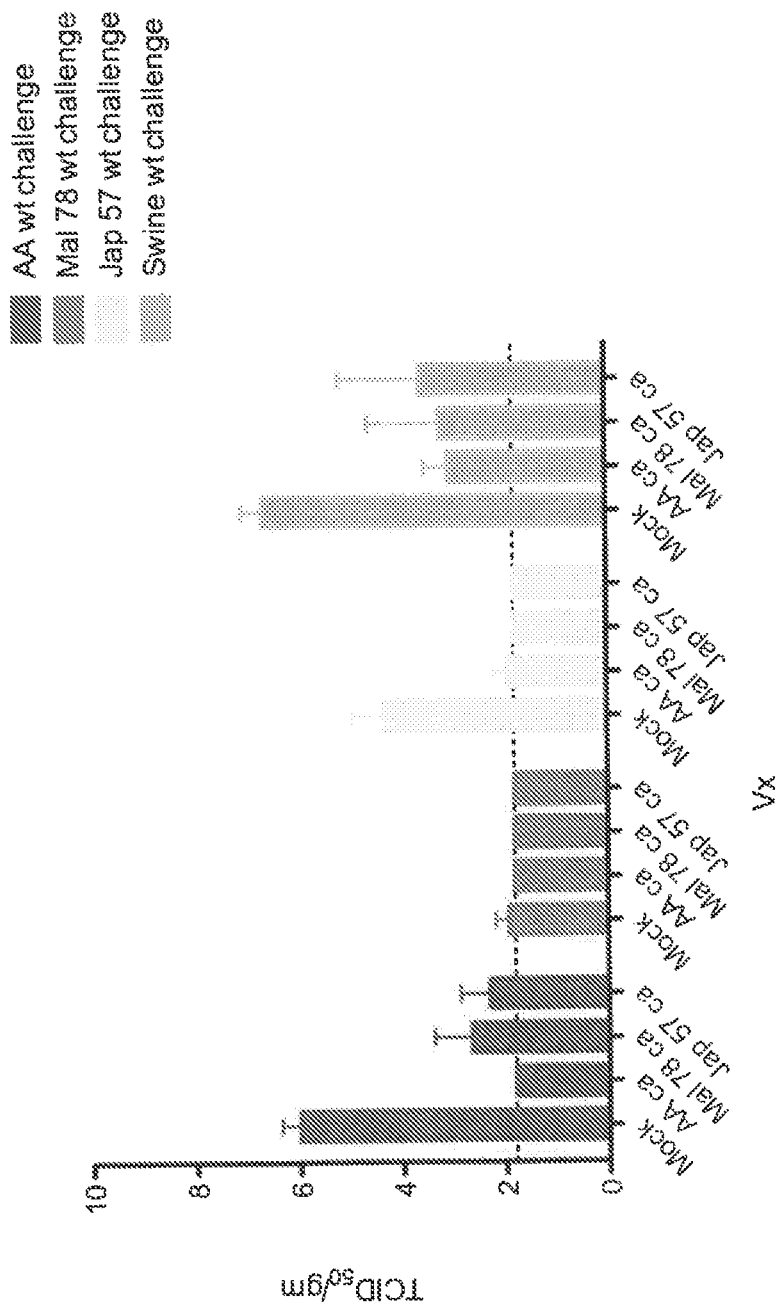
FIG. 4: Replication of H2 wt challenge viruses in NT of mice vaccinated with various indicated H2 vaccine viruses.

FIGS. 3 and 4 show the efficacy of protection conferred by the ca AA, ca A/Japan/57, ca A/mallard/NY/78 and ca A/swine/MO/2006 vaccines in mice. Mice were vaccinated with a single dose of ca reassortant virus vaccine. The mice were then challenged with wt AA, wt A/Japan/57, wt A/mallard/NY/78 and wt A/swine/MO/2006 influenza virus. Three days post challenge lungs and nasal turbinates of the mice were harvested and virus titer in the tissues was determined FIGS. 3 and 4 show efficacy of protection conferred by the recombinant H2 vaccines against homologous and heterologous wild-type H2 viruses in lungs and nasal turbinates, respectively, in mice.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

| SEQUENCES |
|---|
| ca A/Japan/57 |

```
SEQ ID NO: 1 Nucleotide Sequence of ca A/Japan/57 H2
Entire molecule length: 1773 nt
    1 agcaaaagca ggggttatac catagacaac caaaagcaaa acaatggcca 51 tcatttatct cattctcctg ttcacagcag tgagagggga ccagatatgc 101 attggatacc atgccaataa ttccacagag aaggtcgaca caattctaga 151 gcggaacgtc actgtgactc atgccaagga cattcttgag aagacccata 201 acggaaagtt atgcaaacta aacggaatcc ctccacttga actaggggac 251 tgtagcattg ccggatggct ccttggaaat ccagaatgtg ataggcttct
```

-continued

| SEQUENCES |
|---|
| 301 aagtgtgcca gaatggtcct atataatgga gaaagaaaac ccgagagacg |
| 351 gtttgtgtta tccaggcagc ttcaatgatt atgaagaatt gaaacatctc |
| 401 ctcagcagcg tgaaacattt cgagaaagta aagattctgc ccaaagatag |
| 451 atggacacag catacaacaa ctggaggttc acgggcctgc gcggtgtctg |
| 501 gtaatccatc attcttcagg aacatggtct ggctgacaaa gaaggatca |
| 551 gattatccgg ttgccaaagg atcgtacaac aatacaagcg agaacaaat |
| 601 gctaataatt tgggggggtgc accatcccaa tgatgagaca gaacaaagaa |
| 651 cattgtacca gaatgtggga acctatgttt ccgtaggcac atcaacattg |
| 701 aacaaaaggt caaccccaga aatagcaaca aggcctaaag tgaatggaca |
| 751 aggaggtaga atggaattct cttggaccct cttggatatg tgggacacca |
| 801 taaattttga gagtactggt aatctaattg caccagagta tggattcaaa |
| 851 atatcgaaaa gaggtagttc agggatcatg aaaacagaag gaacacttga |
| 901 gaactgtgag accaaatgcc aaactccttt gggagcaata aatacaacat |
| 951 tgccttttca caatgtccac ccactgacaa taggtgagtg ccccaaatat |
| 1001 gtaaaatcgg agaagttggt cttagcaaca ggactaagga atgttcccca |
| 1051 gattgaatca agaggattgt ttggggcaat agctggtttt atagaaggag |
| 1101 gatggcaagg aatggttgat ggttggtatg gataccatca cagcaatgac |
| 1151 cagggatcag ggtatgcagc agacaaagaa tccactcaaa aggcatttga |
| 1201 tggaatcacc aacaaggtaa attctgtgat tgaaaagatg aacacccaat |
| 1251 ttgaagctgt tgggaaagaa ttcagtaact tagagagaag actggagaac |
| 1301 ttgaacaaaa agatggaaga cgggtttcta gatgtgtgga catacaatgc |
| 1351 tgagcttcta gttctgatgg aaaatgagag gacacttgac tttcatgatt |
| 1401 ctaatgtcaa gaatctgtat gataaagtca gaatgcagct gagagacaac |
| 1451 gtcaaagaac taggaaatgg atgttttgaa ttttatcaca aatgtgatga |
| 1501 tgaatgcatg aatagtgtga aaacgggac gtatgattat cccaagtatg |
| 1551 aagaagagtc taaactaaat agaaatgaaa tcaaagggggg aaaattgagc |
| 1601 agcatggggg tttatcaaat ccttgccatt tatgctacag tagcaggttc |
| 1651 tctgtcactg gcaatcatga tggctgggat ctcttctctgg atgtgctcca |
| 1701 acgggtctct gcagtgcagg atctgcatat gattataagt cattttataa |
| 1751 ttaaaaacac ccttgtttct act |

SEQ ID NO: 2 Amino acid sequence of ca A/Japan/57 H2
Entire molecule length: 562 aa
   1 maiiylillf tavrgdqici gyhannstek vdtilernvt vthakdilek 51 thngklckln gipplelgdc siagwllgnp ecdrllsvpe wsyimekenp 101 rdglcypgsf ndyeelkhll ssvkhfekvk ilpkdrwtqh tttggsraca 151 vsgnpsffrn mvwltkkgsd ypvakgsynn tsgeqmliiw gvhhpndete 201 qrtlyqnvgt yvsvgtstln krstpeiatr pkvngqggrm efswtlldmw 251 dtinfestgn liapeygfki skrgssgimk tegtlencet kcqtplgain 301 ttlpfhnvhp ltigecpkyv kseklvlatg lrnvpqiesr glfgaiagfi 351 eggwqgmvdg wygyhhsndq gsgyaadkes tqkafdgitn kvnsviekmn

```
401 tqfeavgkef snlerrlenl nkkmedgfld vwtynaellv lmenertldf 451 hdsnvknlyd kvrmqlrdnv kelgngcfef yhkcddecmn svkngtydyp 501 kyeeesklnr neikgvklss mgvyqilaiy atvagslsla immagisfwm 551 csngslqcri ci
```

SEQ ID NO: 3 Nucleotide Sequence of ca A/Japan/57 N2
Entire molecule length: 1466 nt

```
   1 agcaaaagca ggagtgaaaa tgaatccaaa tcaaaagata ataacaattg 51 gctctgtctc tctcaccatt gaaacagtat gcttcctcat gcagattgcc 101 atcctggcaa ctactgtgac attgcatttt aagcaacatg agtgcgactc 151 ccccgcgagc aaccaagtaa tgccatgtga accaataata atagaaagga 201 acataacaga gatagtgtat ttgaataaca ccaccataga gaaagagatt 251 tgccccgaag tagtggaata cagaaattgg tcaaagccgc aatgtcaaat 301 tacaggattt gcaccttttt ctaaggacaa ttcaatccgg ctttctgctg 351 gtggggacat ttgggtgacg agagaacctt atgtgtcatg cgatcctggc 401 aagtgttatc aatttgcact cgggcagggg accacactag acaacaaaca 451 ttcaaatggc acaatacatg atagaatccc tcatcgaacc ctattaatga 501 atgagttggg tgttccattt catttaggaa ccaaacaagt gtgtgtagca 551 tggtccagct caagttgtca cgatggaaaa gcatggttgc atgtttgtgt 601 cactggggat gatagaaatg caactgctag cttcatttat gacgggaggc 651 ttgtggacag tattggttca tggtctcaaa atatcctcag gacccaggag 701 tcggaatgcg tttgtatcaa tgggacttgc acagtagtaa tgactgatgg 751 aagtgcatca ggaagagccg atactagaat actattcatt aaagagggga 801 aaattgtcca tattagccca ttgtcaggaa gtgctcagca tatagaggag 851 tgttcctgtt accctcgata tcctgacgtc agatgtatct gcagagacaa 901 ctggaaaggc tctaataggc ccgttataga cataaatatg gaagattata 951 gcattgattc cagttatgtg tgctcagggc ttgttggcga cacacccagg 1001 aacgacgaca gctctagcaa tagcaattgc agggatccta caatgagag 1051 agggaatcca ggagtgaaag ctgggccctt gacaatgga gatgatgtat 1101 ggatgggaag aacaatcagc aaagattcac gctcaggtta tgaaactttc 1151 aaagtcattg gtggttggtc cacacctaat tccaaatcgc aggtcaatag 1201 acaggtcata gttgacaaca taattggtc tggttactct ggtatttttct 1251 ctgttgaggg caaaagctgc atcaataggt gcttttatgt ggagttgata 1301 aggggaaggc cacaggagac tagagtatgg tggacctcaa acagtattgt 1351 tgtgttttgt ggcacttcag gtacttatgg aacaggctca tggcctgatg 1401 gggcgaacat caatttcatg cctatataag ctttcgcaat tttagaaaaa 1451 actccttgtt tctact
```

SEQ ID NO: 4 Amino acid sequence of ca A/Japan/57 N2
Entire molecule length: 471 aa

```
   1 mnpnqkiiti gsysltietv cflmqiaila ttvtlhfkqh ecdspasnqv 51 mpcepiiier niteivylnn ttiekeicpe vveyrnwskp qcqitgfapf
```

-continued

| SEQUENCES |
|---|
| 101 skdnsirlsa ggdiwvtrep yvscdpgkcy qfalgqgttl dnkhsngtih |
| 151 driphrtllm nelgvpfhlg tkqvcvawss sschdgkawl hvcvtgddrn |
| 201 atasfiydgr lvdsigswsq nilrtqesec vcingtctvv mtdgsasgra |
| 251 dtrilfikeg kivhisplsg saqhieecsc yprypdvrci crdnwkgsnr |
| 301 pvidinmedy sidssyvcsg lvgdtprndd sssnsncrdp nnergnpgvk |
| 351 gwafdngddv wmgrtiskds rsgyetfkvi ggwstpnsks qvnrqvivdn |
| 401 nnwsgysgif svegkscinr cfyvelirgr pqetrvwwts nsivvfcgts |
| 451 gtygtgswpd ganinfmpi |
| ca A/swine/MO/2006 |

SEQ ID NO: 5 Nucleotide Sequence of ca A/swine/MO/2006 H2
Entire molecule length: 1772 nt

```
   1 agcaaaagca ggggttatac catagacaac cgaacaaaga caatgaccat
  51 cacttttctc atcctcctgt tcacagtagt gaaaggggac caaatatgca
 101 tcggatacca tgccaacaat tccacagaaa aagttgacac aatcttggaa
 151 cgaaacgtca ccgtgactca tgccaagaac attcttgaaa gacgcataa
 201 tggaaagttg tgcagattga gtggaatccc tccattggaa ctggggggatt
 251 gcagcattgc aggttggctc cttggaaatc cggaatgtga ccggctctta
 301 agtgtacctg aatggtccta tatagtggaa aaggaaaacc cggtgaatgg
 351 tctgtgctat ccaggcagtt caatgatta tgaggaattg aaacatcttc
 401 tcaccagtgt gacacacttt gagaaagtta agattctgcc cagagatcaa
 451 tggacccagc acacaacaac tggtggttct cgggcctgtg cagtatctgg
 501 aaacccgtca ttctttagga acatggtttg cttacaaag aaagggtcaa
 551 actactcaat tgctaaaagg tcatacaaca acacaagtgg ggagcaaatg
 601 ctggtaatat gggggataca tcaccccaat gacgatgcgg aacagaggac
 651 actgtaccag aatgtgggaa catatgtttc cgttggaaca tcaacactaa
 701 ataagaggtc aatccctgaa atagcaacaa ggcccaaagt caatggacag
 751 ggaggaagaa tggaattctc ttggactcta ttggagacat gggatgtcat
 801 aaattttgag agcactggta atttaattgc accagaatac ggattcaaaa
 851 tatcaaagag aggaagctca gaattatga agacagaaa atacttgaa
 901 aattgtgaaa ccaaatgtca gacccccttg ggggcaataa atacaacatt
 951 gcccttcac aacattcacc cattgacaat aggtgagtgc cccaagtatg
1001 taaagtcaga tagactgatt ttggcgacag gagtaagaaa tgtcccccag
1051 attgaatcaa ggggattgtt tggagcaata gctgggttta tagaaggcgg
1101 atggcaaggg atggttgatg gctggtatgg gtaccatcac agcaatgatc
1151 aaggatcagg atatgcagca gacaaagaat ccactcaaaa ggcaattgat
1201 gggataacta acaaagtaaa ttctgtgatt gaaaagatga acactcagtt
1251 tgaggctgtt gggaaagagt tcaacaacct agagagaagg ctggaaaact
1301 taaataaaaa gatggaagat ggattattg atgtatggac ataataatgcc
1351 gaactcctag ttctaatgga aaatgagagg acacttgatt ccatgattc
1401 taatgtgaag aatctgtacg ataaggtcag aatgcaattg agagacaatg
```

```
1451 ctaaggaaat agggaacgga tgctttgagt tttatcataa atgtgatgat 1501 gaatgcatga atagtgtcag gaatgggaca tatgattatc ccaaatatga 1551 ggaagagtcc aagctgaaca ggaacgaaat caaaggagtg aaattgagca 1601 atatgggggt ttatcaaata cttgctatat acgctacagt tgcaggctct 1651 ttgtcactgg caatcatgat agctgggatt tctttctgga tgtgttctaa 1701 tgggtctctg caatgcagaa tttgcatatg actgtaagtc aatttgtaat 1751 taaaaacacc cttgtttcta ct
```

SEQ ID NO: 6 Amino acid sequence of ca A/swine/MO/2006 H2
Entire molecule length: 562 aa
```
    1 mtitflillf tvvkgdqici gyhannstek vdtilernvt vthaknilek 51 thngklcrls gipplelgdc siagwllgnp ecdrllsvpe wsyivekenp 101 vnglcypgsf ndyeelkhll tsvthfekvk ilprdqwtqh tttggsraca 151 vsgnpsffrn mvwltkkgsn ysiakrsynn tsgeqmlviw gihhpnddae 201 qrtlyqnvgt yvsvgtstln krsipeiatr pkvngqggrm efswtlletw 251 dvinfestgn liapeygfki skrgssgimk tekilencet kcqtplgain 301 ttlpfhnihp ltigecpkyv ksdrlilatg vrnvpqiesr glfgaiagfi 351 eggwqgmvdg wygyhhsndq gsgyaadkes tqkaidgitn kvnsviekmn 401 tqfeavgkef nnlerrlenl nkkmedgfid vwtynaellv lmenertldf 451 hdsnvknlyd kvrmqlrdna keigngcfef yhkcddecmn svrngtydyp 501 kyeeesklnr neikgvklsn mgvyqilaiy atvagslsla imiagisfwm 551 csngslqcri ci
```

SEQ ID NO: 7 Nucleotide Sequence of ca A/swine/MO/2006 N3
Entire molecule length: 1453 nt
```
    1 agcaaaagca ggtgcgagat gaatccgaat cagaagataa taacaatcgg 51 ggtagtgaat accactctgt caacaatagc ccttctcatt ggagtgggaa 101 acttaatttt caacacagtc atacatgaga aaataggaga ccatcaaata 151 gtgacctatc aacaataac gaccccctgca gtaccgaact gcagtgacac 201 tataataaca tacaataaca ctgtgataaa caacataaca acaacaataa 251 taactgaaga agaaaggcct ttcaagtctc cactaccgct gtgccccttc 301 agaggattct tccctttca caaggacaat gcaatacgac tgggtgaaaa 351 caaagacgtc atagtcacaa gagagcctta tgttagctgc gataatgaca 401 actgctggtc ctttgctctc acacaaggag cattgctagg gaccaaacat 451 agcaatggga ccattaaaga caggacacca tataggtctc taattcgttt 501 cccaatagga acagctccag tactaggaaa ttataaagag atatgcattg 551 cttggtcgag cagcagttgc tttgacggga agagtggat gcatgtgtgc 601 atgacaggga acgataatga tgcaagtgcc cagataatat atggagggag 651 aatgacagac tccattaaat catggagaaa ggacatacta agaactcagg 701 agtctgaatg ccaatgcatt gacgggactt gtgttgttgc tgtcacagat 751 ggccctgctg ctaatagtgc agattacagg gtttactgga tacgggaggg 801 aaaaataata aagtatgaaa atgttcccaa acaaagata caacacttag
```

| SEQUENCES |
|---|
| 851 aagaatgttc ctgctatgtg gacattgatg tttactgtat atgtagggac |
| 901 aattggaagg gctctaacag accttggatg agaatcaaca acgagactat |
| 951 actggaaaca gggtatgtat gtagtaaatt ccactcagac accccaggc |
| 1001 ccgctgaccc ttcaacaatg tcatgtgact ccccaagcaa tgtcaatgga |
| 1051 ggacccggag tgaaggggtt tggtttcaaa gctggcgatg atgtatggtt |
| 1101 aggtagaaca gtgtcgacta gtggtagatc gggctttgaa attatcaaag |
| 1151 ttacagaagg gtggatcaac tctcctaacc atgtcaaatc aattacacaa |
| 1201 acactagtgc caaacaatga ctggtcaggc tattccggta gcttcattgt |
| 1251 caaagccaag gactgttttc agccctgttt ttatgttgag cttatacgag |
| 1301 ggaggcccaa caagaatgat gacgtctctt ggacaagtaa tagtatagtt |
| 1351 actttctgtg gactagacaa tgaacctgga tcgggaaatt ggccagatgg |
| 1401 ttctaacatt gggtttatgc ccaagtaata gaaaaaagca ccttgtttct |
| 1451 act |

SEQ ID NO: 8 Amino acid sequence of ca A/swine/MO/2006 N2
Entire molecule length: 469 aa

```
  1 mnpnqkiiti gvvnttlsti alligvgnli fntvihekig dhqivtypti
 51 ttpavpncsd tiitynntvi nnitttiite eerpfksplp lcpfrgffpf
101 hkdnairlge nkdvivtrep yvscdndncw sfaltqgall gtkhsngtik
151 drtpyrslir fpigtapvlg nykeiciaws ssscfdgkew mhvcmtgndn
201 dasaqiiygg rmtdsikswr kdilrtqese cqcidgtcvv avtdgpaans
251 adyrvywire gkiikyenvp ktkiqhleec scyvdidvyc icrdnwkgsn
301 rpwmrinnet iletgyvcsk fhsdtprpad pstmscdsps nvnggpgvkg
351 fgfkagddvw lgrtvstsgr sgfeiikvte gwinspnhvk sitqtlvpnn
401 dwsgysgsfi vkakdcfqpc fyvelirgrp nkndvswts nsivtfcgld
451 nepgsgnwpd gsnigfmpk
```

---

What is claimed is:

1. A reassortant influenza virus comprising a polynucleotide selected from the group consisting of:
   (a) a polynucleotide comprising SEQ ID NO:7, or a complement thereof; and
   (b) a polynucleotide comprising a nucleotide sequence that encodes a polypeptide comprising the amino acid sequence of SEQ ID NO:8.

2. The reassortant influenza virus of claim 1, which is a 6:2 reassortant influenza virus that includes 6 internal genome segments from one or more donor viruses.

3. The reassortant influenza virus of claim 2, wherein the one or more donor viruses include an A/Ann Arbor/6/60 virus.

4. The reassortant influenza virus of claim 3, which comprises 6 internal genome segments from an A/Ann Arbor/6/60 virus.

5. The reassortant influenza virus of claim 2, which comprises 6 internal genome segments from one or more donor viruses other than an A/Ann Arbor/6/60 virus.

6. The reassortant influenza virus of claim 5, wherein the one or more donor viruses include a PR8 virus.

7. The reassortant influenza virus of claim 5, wherein the one or more donor viruses include an A/Leningrad/17 virus.

8. The reassortant influenza virus of claim 2, wherein the internal genome segments of the one or more donor viruses confer one or more of the following properties to the reassortant virus: temperature sensitive virus, cold adapted virus, and attenuated virus.

9. A method, comprising: administering to an individual an immunologically effective amount of the reassortant influenza virus of claim 1 in a physiologically effective carrier in an amount effective for stimulating the immune system of the individual to produce a protective immune response against an influenza virus.

10. A method, comprising: administering to a subject the reassortant influenza virus of claim 1 in an amount effective to produce a prophylactic or therapeutic immunogenic response against an influenza viral infection in the subject.

11. An immunogenic composition comprising an immunologically effective amount of the reassortant influenza virus of claim 1.

12. A live attenuated influenza vaccine comprising the immunogenic composition of claim 11.

13. A split virus or killed virus vaccine comprising the immunogenic composition of claim 11.

14. A method, comprising: administering to an individual the immunogenic composition of claim 11, thereby stimulating the immune system of the individual to produce a protective immune response against an influenza virus.

15. A method for producing a reassortant influenza virus, comprising:
   (a) introducing into a population of host cells a plurality of vectors comprising nucleic acid sequences corresponding to:
      i) at least 6 internal genome segments from a donor virus and a genome segment encoding an immunogenic influenza surface antigen; or
      ii) at least 6 internal genome segments from a donor virus, wherein said donor virus has one or more phenotypic attributes selected from the group consisting of: attenuated, cold adapted and temperature sensitive; and a genome segment encoding an immunogenic influenza surface antigen;
   wherein the genome segment encoding the immunogenic influenza surface antigen is selected from the group consisting of:
      (1) a polynucleotide comprising SEQ ID NO:7, or a complement thereof; and (2) a polynucleotide comprising a nucleotide sequence that encodes a polypeptide comprising the amino acid sequence of SEQ ID NO:8;

(b) culturing the population of host cells in a suitable culture medium under conditions permitting expression of the polynucleotide; and (c) isolating the reassortant influenza virus from the medium or the population of host cells.

16. The method of claim 15, wherein the donor virus is an A/Ann Arbor/6/60 virus.

17. The method of claim 15, wherein the donor virus is a virus other than A/Ann Arbor/6/60.

18. The method of claim 15, wherein the culturing in part (b) is performed at a temperature less than or equal to 35° C.

19. An immunogenic composition comprising an immunologically effective amount of the reassortant influenza virus produced by the method of claim 15.

20. A method, comprising: administering to an individual an immunologically effective amount of the reassortant influenza virus produced by the method of claim 15 in a physiologically effective carrier to stimulate the immune system of the individual to produce a protective immune response against influenza virus.

\* \* \* \* \*

SEQUENCE LISTING

<160> NUMBER OF SEQ ID NOS: 9

<210> SEQ ID NO 1
<211> LENGTH: 1773
<212> TYPE: DNA
<213> ORGANISM: Influenza A virus

<400> SEQUENCE: 1

| agcaaaagca ggggttatac catagacaac caaaagcaaa acaatggcca tcatttatct | 60 |
| cattctcctg ttcacagcag tgagagggga ccagatatgc attggatacc atgccaataa | 120 |
| ttccacagag aaggtcgaca caattctaga gcggaacgtc actgtgactc atgccaagga | 180 |
| cattcttgag aagacccata acggaaagtt atgcaaacta acggaatcc ctccacttga | 240 |
| actaggggac tgtagcattg ccggatggct ccttggaaat ccagaatgtg ataggcttct | 300 |
| aagtgtgcca gaatggtcct atataatgga gaaagaaaac ccgagagacg gtttgtgtta | 360 |
| tccaggcagc ttcaatgatt atgaagaatt gaaacatctc ctcagcagcg tgaaacattt | 420 |

```
cgagaaagta aagattctgc ccaaagatag atggacacag catacaacaa ctggaggttc    480
acgggcctgc gcggtgtctg gtaatccatc attcttcagg aacatggtct ggctgacaaa    540
gaaaggatca gattatccgg ttgccaaagg atcgtacaac aatacaagcg gagaacaaat    600
gctaataatt tggggggtgc accatcccaa tgatgagaca gaacaaagaa cattgtacca    660
gaatgtggga acctatgttt ccgtaggcac atcaacattg aacaaaaggt caaccccaga    720
aatagcaaca aggcctaaag tgaatggaca aggaggtaga atggaattct cttggaccct    780
cttggatatg tgggacacca taaattttga gagtactggt aatctaattg caccagagta    840
tggattcaaa atatcgaaaa gaggtagttc agggatcatg aaaacagaag gaacacttga    900
gaactgtgag accaaatgcc aaactccttt gggagcaata aatacaacat tgccttttca    960
caatgtccac ccactgacaa taggtgagtg ccccaaatat gtaaaatcgg agaagttggt   1020
cttagcaaca ggactaagga atgttcccca gattgaatca agaggattgt ttggggcaat   1080
agctggtttt atagaaggag gatggcaagg aatggttgat ggttggtatg gataccatca   1140
cagcaatgac cagggatcag ggtatgcagc agacaaagaa tccactcaaa aggcatttga   1200
tggaatcacc aacaaggtaa attctgtgat tgaaaagatg aacacccaat ttgaagctgt   1260
tgggaaagaa ttcagtaact tagagagaag actggagaac ttgaacaaaa agatggaaga   1320
cgggtttcta gatgtgtgga catacaatgc tgagcttcta gttctgatgg aaaatgagag   1380
gacacttgac tttcatgatt ctaatgtcaa gaatctgtat gataaagtca gaatgcagct   1440
gagagacaac gtcaaagaac taggaaatgg atgttttgaa ttttatcaca aatgtgatga   1500
tgaatgcatg aatagtgtga aaaacgggac gtatgattat cccaagtatg aagaagagtc   1560
taaactaaat agaaatgaaa tcaaaggggt aaaattgagc agcatggggg tttatcaaat   1620
ccttgccatt tatgctacag tagcaggttc tctgtcactg gcaatcatga tggctgggat   1680
ctctttctgg atgtgctcca acgggtctct gcagtgcagg atctgcatat gattataagt   1740
cattttataa ttaaaaacac ccttgtttct act                                1773
```

<210> SEQ ID NO 2
<211> LENGTH: 562
<212> TYPE: PRT
<213> ORGANISM: Influenza A virus

<400> SEQUENCE: 2

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
```

-continued

```
                130                 135                 140
Gly Ser Arg Ala Cys Ala Val Ser Gly Asn Pro Ser Phe Phe Arg Asn
145                 150                 155                 160
Met Val Trp Leu Thr Lys Lys Gly Ser Asp Tyr Pro Val Ala Lys Gly
                165                 170                 175
Ser Tyr Asn Asn Thr Ser Gly Glu Gln Met Leu Ile Ile Trp Gly Val
                180                 185                 190
His His Pro Asn Asp Glu Thr Glu Gln Arg Thr Leu Tyr Gln Asn Val
                195                 200                 205
Gly Thr Tyr Val Ser Val Gly Thr Ser Thr Leu Asn Lys Arg Ser Thr
                210                 215                 220
Pro Glu Ile Ala Thr Arg Pro Lys Val Asn Gly Gln Gly Gly Arg Met
225                 230                 235                 240
Glu Phe Ser Trp Thr Leu Leu Asp Met Trp Asp Thr Ile Asn Phe Glu
                245                 250                 255
Ser Thr Gly Asn Leu Ile Ala Pro Glu Tyr Gly Phe Lys Ile Ser Lys
                260                 265                 270
Arg Gly Ser Ser Gly Ile Met Lys Thr Glu Gly Thr Leu Glu Asn Cys
                275                 280                 285
Glu Thr Lys Cys Gln Thr Pro Leu Gly Ala Ile Asn Thr Thr Leu Pro
290                 295                 300
Phe His Asn Val His Pro Leu Thr Ile Gly Glu Cys Pro Lys Tyr Val
305                 310                 315                 320
Lys Ser Glu Lys Leu Val Leu Ala Thr Gly Leu Arg Asn Val Pro Gln
                325                 330                 335
Ile Glu Ser Arg Gly Leu Phe Gly Ala Ile Ala Gly Phe Ile Glu Gly
                340                 345                 350
Gly Trp Gln Gly Met Val Asp Gly Trp Tyr Gly Tyr His His Ser Asn
                355                 360                 365
Asp Gln Gly Ser Gly Tyr Ala Ala Asp Lys Glu Ser Thr Gln Lys Ala
                370                 375                 380
Phe Asp Gly Ile Thr Asn Lys Val Asn Ser Val Ile Glu Lys Met Asn
385                 390                 395                 400
Thr Gln Phe Glu Ala Val Gly Lys Glu Phe Ser Asn Leu Glu Arg Arg
                405                 410                 415
Leu Glu Asn Leu Asn Lys Lys Met Glu Asp Gly Phe Leu Asp Val Trp
                420                 425                 430
Thr Tyr Asn Ala Glu Leu Leu Val Leu Met Glu Asn Glu Arg Thr Leu
                435                 440                 445
Asp Phe His Asp Ser Asn Val Lys Asn Leu Tyr Asp Lys Val Arg Met
                450                 455                 460
Gln Leu Arg Asp Asn Val Lys Glu Leu Gly Asn Gly Cys Phe Glu Phe
465                 470                 475                 480
Tyr His Lys Cys Asp Asp Glu Cys Met Asn Ser Val Lys Asn Gly Thr
                485                 490                 495
Tyr Asp Tyr Pro Lys Tyr Glu Glu Glu Ser Lys Leu Asn Arg Asn Glu
                500                 505                 510
Ile Lys Gly Val Lys Leu Ser Ser Met Gly Val Tyr Gln Ile Leu Ala
                515                 520                 525
Ile Tyr Ala Thr Val Ala Gly Ser Leu Ser Leu Ala Ile Met Met Ala
                530                 535                 540
Gly Ile Ser Phe Trp Met Cys Ser Asn Gly Ser Leu Gln Cys Arg Ile
545                 550                 555                 560
```

Cys Ile

<210> SEQ ID NO 3
<211> LENGTH: 1466
<212> TYPE: DNA
<213> ORGANISM: Influenza A virus

<400> SEQUENCE: 3

| | |
|---|---|
| agcaaaagca ggagtgaaaa tgaatccaaa tcaaaagata taacaattg gctctgtctc | 60 |
| tctcaccatt gaaacagtat gcttcctcat gcagattgcc atcctggcaa ctactgtgac | 120 |
| attgcatttt aagcaacatg agtgcgactc ccccgcgagc aaccaagtaa tgccatgtga | 180 |
| accaataata atagaaagga acataacaga gatagtgtat ttgaataaca ccaccataga | 240 |
| gaaagagatt gccccgaagt agtggaata cagaaaattgg tcaaagccgc aatgtcaaat | 300 |
| tacaggattt gcaccttttt ctaaggacaa ttcaatccgg ctttctgctg gtggggacat | 360 |
| ttgggtgacg agagaacctt atgtgtcatg cgatcctggc aagtgttatc aatttgcact | 420 |
| cgggcagggg accacactag acaacaaaca ttcaaatggc acaatacatg atagaatccc | 480 |
| tcatcgaacc ctattaatga atgagttggg tgttccattt catttaggaa ccaaacaagt | 540 |
| gtgtgtagca tggtccagct caagttgtca cgatggaaaa gcatggttgc atgtttgtgt | 600 |
| cactggggat gatagaaatg caactgctag cttcatttat gacgggaggc ttgtggacag | 660 |
| tattggttca tggtctcaaa atatcctcag gacccaggag tcggaatgcg tttgtatcaa | 720 |
| tgggacttgc acagtagtaa tgactgatgg aagtgcatca ggaagagccg atactagaat | 780 |
| actattcatt aaagagggga aaattgtcca tattagccca ttgtcaggaa gtgctcagca | 840 |
| tatagaggag tgttcctgtt accctcgata tcctgacgtc agatgtatct gcagagacaa | 900 |
| ctggaaaggc tctaataggc ccgttataga cataaatatg gaagattata gcattgattc | 960 |
| cagttatgtg tgctcagggc ttgttggcga cacacccagg aacgacgaca gctctagcaa | 1020 |
| tagcaattgc agggatccta acaatgagag agggaatcca ggagtgaaag ctgggcctt | 1080 |
| tgacaatgga gatgatgtat ggatgggaag aacaatcagc aaagattcac gctcaggtta | 1140 |
| tgaaactttc aaagtcattg gtggttggtc cacacctaat tccaaatcgc aggtcaatag | 1200 |
| acaggtcata gttgacaaca taattggtg tggttactct ggtattttct ctgttgaggg | 1260 |
| caaaagctgc atcaataggt gctttttatgt ggagttgata aggggaaggc cacaggagac | 1320 |
| tagagtatgg tggacctcaa acagtattgt tgtgttttgt ggcacttcag gtacttatgg | 1380 |
| aacaggctca tggcctgatg gggcgaacat caatttcatg cctatataag ctttcgcaat | 1440 |
| tttagaaaaa actccttgtt tctact | 1466 |

<210> SEQ ID NO 4
<211> LENGTH: 469
<212> TYPE: PRT
<213> ORGANISM: Influenza A virus

<400> SEQUENCE: 4

Met Asn Pro Asn Gln Lys Ile Ile Thr Ile Gly Ser Val Ser Leu Thr
1               5                   10                  15

Ile Glu Thr Val Cys Phe Leu Met Gln Ile Ala Ile Leu Ala Thr Thr
                20                  25                  30

Val Thr Leu His Phe Lys Gln His Glu Cys Asp Ser Pro Ala Ser Asn
            35                  40                  45

Gln Val Met Pro Cys Glu Pro Ile Ile Ile Glu Arg Asn Ile Thr Glu

```
                50              55              60
Ile Val Tyr Leu Asn Asn Thr Thr Ile Glu Lys Glu Ile Cys Pro Glu
65                      70                  75                  80

Val Val Glu Tyr Arg Asn Trp Ser Lys Pro Gln Cys Gln Ile Thr Gly
                    85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Gly Lys
                115                 120                 125

Cys Tyr Gln Phe Ala Leu Gly Gln Gly Thr Thr Leu Asp Asn Lys His
                130                 135                 140

Ser Asn Gly Thr Ile His Asp Arg Ile Pro His Arg Thr Leu Leu Met
145                 150                 155                     160

Asn Glu Leu Gly Val Pro Phe His Leu Gly Thr Lys Gln Val Cys Val
                    165                 170                 175

Ala Trp Ser Ser Ser Cys His Asp Gly Lys Ala Trp Leu His Val
                180                 185                 190

Cys Val Thr Gly Asp Asp Arg Asn Ala Thr Ala Ser Phe Ile Tyr Asp
                    195                 200                 205

Gly Arg Leu Val Asp Ser Ile Gly Ser Trp Ser Gln Asn Ile Leu Arg
                    210                 215                 220

Thr Gln Glu Ser Glu Cys Val Cys Ile Asn Gly Thr Cys Thr Val Val
225                 230                 235                     240

Met Thr Asp Gly Ser Ala Ser Gly Arg Ala Asp Thr Arg Ile Leu Phe
                    245                 250                 255

Ile Lys Glu Gly Lys Ile Val His Ile Ser Pro Leu Ser Gly Ser Ala
                    260                 265                 270

Gln His Ile Glu Glu Cys Ser Cys Tyr Pro Arg Tyr Pro Asp Val Arg
                    275                 280                 285

Cys Ile Cys Arg Asp Asn Trp Lys Gly Ser Asn Arg Pro Val Ile Asp
                290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Ser Ser Ser Asn Ser Asn
                    325                 330                 335

Cys Arg Asp Pro Asn Asn Glu Arg Gly Asn Pro Gly Val Lys Gly Trp
                340                 345                 350

Ala Phe Asp Asn Gly Asp Asp Val Trp Met Gly Arg Thr Ile Ser Lys
                355                 360                 365

Asp Ser Arg Ser Gly Tyr Glu Thr Phe Lys Val Ile Gly Gly Trp Ser
370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                    405                 410                 415

Cys Ile Asn Arg Cys Phe Tyr Val Glu Leu Ile Arg Gly Arg Pro Gln
                420                 425                 430

Glu Thr Arg Val Trp Trp Thr Ser Asn Ser Ile Val Val Phe Cys Gly
                435                 440                 445

Thr Ser Gly Thr Tyr Gly Thr Gly Ser Trp Pro Asp Gly Ala Asn Ile
                450                 455                 460

Asn Phe Met Pro Ile
465
```

-continued

<210> SEQ ID NO 5
<211> LENGTH: 1772
<212> TYPE: DNA
<213> ORGANISM: Influenza A virus

<400> SEQUENCE: 5
agcaaaagca ggggttatac catagacaac cgaacaaaga caatgaccat cacttttctc 60
atcctcctgt tcacagtagt gaaaggggac caaatatgca tcggatacca tgccaacaat 120
tccacagaaa aagttgacac aatcttggaa cgaaacgtca ccgtgactca tgccaagaac 180
attcttgaaa agacgcataa tggaaagttg tgcagattga gtggaatccc tccattggaa 240
ctgggggatt gcagcattgc aggttggctc cttggaaatc cggaatgtga ccggctctta 300
agtgtacctg aatggtccta tatagtggaa aaggaaaacc cggtgaatgg tctgtgctat 360
ccaggcagtt tcaatgatta tgaggaattg aaacatcttc tcaccagtgt gacacacttt 420
gagaaagtta agattctgcc cagagatcaa tggacccagc acacaacaac tggtggttct 480
cgggcctgtg cagtatctgg aaacccgtca ttctttagga acatggtttg gcttacaaag 540
aaagggtcaa actactcaat tgctaaaagg tcatacaaca acacaagtgg ggagcaaatg 600
ctggtaatat gggggataca tcaccccaat gacgatgcgg aacagaggac actgtaccag 660
aatgtgggaa catatgtttc cgttggaaca tcaacactaa ataagaggtc aatccctgaa 720
atagcaacaa ggcccaaagt caatggacag ggaggaagaa tggaattctc ttggactcta 780
ttggagacat gggatgtcat aaattttgag agcactggta atttaattgc accagaatac 840
ggattcaaaa tatcaaagag aggaagctca ggaattatga agacagagaa aatacttgaa 900
aattgtgaaa ccaaatgtca gaccccttg ggggcaataa atacaacatt gccctttcac 960
aacattcacc cattgacaat aggtgagtgc cccaagtatg taaagtcaga tagactgatt 1020
ttggcgacag gagtaagaaa tgtcccccag attgaatcaa ggggattgtt tggagcaata 1080
gctgggttta tagaaggcgg atggcaaggg atggttgatg gctggtatgg gtaccatcac 1140
agcaatgatc aaggatcagg atatgcagca gacaaagaat ccactcaaaa ggcaattgat 1200
gggataacta acaaagtaaa ttctgtgatt gaaaagatga acactcagtt tgaggctgtt 1260
gggaaagagt tcaacaacct agagagaagg ctggaaaact taaataaaaa gatggaagat 1320
ggatttattg atgtatggac atataatgcc gaactcctag ttctaatgga aaatgagagg 1380
acacttgatt tccatgattc taatgtgaag aatctgtacg ataaggtcag aatgcaattg 1440
agagacaatg ctaaggaaat agggaacgga tgctttgagt tttatcataa atgtgatgat 1500
gaatgcatga atagtgtcag gaatgggaca tatgattatc ccaaatatga ggaagagtcc 1560
aagctgaaca ggaacgaaat caaaggagtg aaattgagca atatggggt ttatcaaata 1620 cttgctatat acgctacagt tgcaggctct ttgtcactgg caatcatgat agctgggatt 1680
tctttctgga tgtgttctaa tgggtctctg caatgcagaa tttgcatatg actgtaagtc 1740
aatttgtaat taaaaacacc cttgtttcta ct 1772

<210> SEQ ID NO 6
<211> LENGTH: 562
<212> TYPE: PRT
<213> ORGANISM: Influenza A virus

<400> SEQUENCE: 6

Met Thr Ile Thr Phe Leu Ile Leu Leu Phe Thr Val Val Lys Gly Asp
1 5 10 15

```
Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asn Ile Leu
        35                  40                  45

Glu Lys Thr His Asn Gly Lys Leu Cys Arg Leu Ser Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Val Glu
                85                  90                  95

Lys Glu Asn Pro Val Asn Gly Leu Cys Tyr Pro Gly Ser Phe Asn Asp
            100                 105                 110

Tyr Glu Glu Leu Lys His Leu Leu Thr Ser Val Thr His Phe Glu Lys
        115                 120                 125

Val Lys Ile Leu Pro Arg Asp Gln Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Ser Ile Ala Lys Arg
                165                 170                 175

Ser Tyr Asn Asn Thr Ser Gly Glu Gln Met Leu Val Ile Trp Gly Ile
            180                 185                 190

His His Pro Asn Asp Asp Ala Glu Gln Arg Thr Leu Tyr Gln Asn Val
        195                 200                 205

Gly Thr Tyr Val Ser Val Gly Thr Ser Thr Leu Asn Lys Arg Ser Ile
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Glu Thr Trp Asp Val Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Lys Ile Leu Glu Asn Cys
        275                 280                 285

Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320

Lys Ser Asp Arg Leu Ile Leu Ala Thr Gly Val Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Arg Arg
                405                 410                 415

Leu Glu Asn Leu Asn Lys Lys Met Glu Asp Gly Phe Ile Asp Val Trp
            420                 425                 430
```

```
Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Lys Val Arg Met
        450                 455                 460

Gln Leu Arg Asp Asn Ala Lys Glu Ile Gly Asn Gly Cys Phe Glu Phe
465                 470                 475                 480

Tyr His Lys Cys Asp Asp Glu Cys Met Asn Ser Val Arg Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Asn Met Gly Val Tyr Gln Ile Leu Ala
            515                 520                 525

Ile Tyr Ala Thr Val Ala Gly Ser Leu Ser Leu Ala Ile Met Ile Ala
        530                 535                 540

Gly Ile Ser Phe Trp Met Cys Ser Asn Gly Ser Leu Gln Cys Arg Ile
545                 550                 555                 560

Cys Ile

<210> SEQ ID NO 7
<211> LENGTH: 1453
<212> TYPE: DNA
<213> ORGANISM: Influenza A virus

<400> SEQUENCE: 7
agcaaaagca ggtgcgagat gaatccgaat cagaagataa taacaatcgg ggtagtgaat      60
accactctgt caacaatagc ccttctcatt ggagtgggaa acttaatttt caacacagtc     120
atacatgaga aataggaga ccatcaaata gtgacctatc aacaataac gaccccctgca     180
gtaccgaact gcagtgacac tataataaca tacaataaca ctgtgataaa aacataaca     240
acaacaataa taactgaaga agaaaggcct ttcaagtctc cactaccgct gtgccccttc     300
agaggattct tccctttca caaggacaat gcaatacgac tgggtgaaaa caaagacgtc     360
atagtcacaa gagagcctta tgttagctgc gataatgaca actgctggtc ctttgctctc     420
acacaaggag cattgctagg gaccaaacat agcaatggga ccattaaaga caggacacca     480
tataggtctc taattcgttt cccaatagga acagctccag tactaggaaa ttataaagag     540
atatgcattg cttggtcgag cagcagttgc tttgacggga agagtggat gcatgtgtgc     600
atgacaggga acgataatga tgcaagtgcc cagataatat atggagggag aatgacagac     660
tccattaaat catggagaaa ggacatacta agaactcagg agtctgaatg ccaatgcatt     720
gacgggactt gtgttgttgc tgtcacagat ggccctgctg ctaatagtgc agattacagg     780
gtttactgga tacgggaggg aaaaataata aagtatgaaa atgttcccaa aacaaagata     840
caacacttag aagaatgttc ctgctatgtg gacattgatg tttactgtat atgtagggac     900
aattggaagg gctctaacag accttggatg agaatcaaca cgagactat actgaaaaca     960
gggtatgtat gtagtaaatt ccactcagac accccaggc cgctgaccc ttcaacaatg    1020
tcatgtgact ccccaagcaa tgtcaatgga ggacccggag tgaaggggtt tggtttcaaa    1080
gctggcgatg atgtatggtt aggtagaaca gtgtcgacta gtggtagatc gggctttgaa    1140
attatcaaag ttacagaagg gtggatcaac tctcctaacc atgtcaaatc aattacacaa    1200
acactagtgc aaacaatga ctggtcaggc tattccggta gcttcattgt caaagccaag    1260
gactgttttt cagccctgtt ttatgttgag cttatacgag ggaggcccaa caagaatgat    1320
gacgtctctt ggacaagtaa tagtatagtt actttctgtg gactagacaa tgaacctgga    1380
```

```
tcgggaaatt ggccagatgg ttctaacatt gggtttatgc ccaagtaata gaaaaaagca    1440
ccttgtttct act                                                       1453
```

<210> SEQ ID NO 8
<211> LENGTH: 469
<212> TYPE: PRT
<213> ORGANISM: Influenza A virus

<400> SEQUENCE: 8

```
Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
            20                  25                  30

Thr Val Ile His Glu Lys Ile Gly Asp His Gln Ile Val Thr Tyr Pro
        35                  40                  45

Thr Ile Thr Thr Pro Ala Val Pro Asn Cys Ser Asp Thr Ile Ile Thr
    50                  55                  60

Tyr Asn Asn Thr Val Ile Asn Asn Ile Thr Thr Ile Ile Thr Glu
65                  70                  75                  80

Glu Glu Arg Pro Phe Lys Ser Pro Leu Pro Leu Cys Pro Phe Arg Gly
                85                  90                  95

Phe Phe Pro Phe His Lys Asp Asn Ala Ile Arg Leu Gly Glu Asn Lys
            100                 105                 110

Asp Val Ile Val Thr Arg Glu Pro Tyr Val Ser Cys Asp Asn Asp Asn
        115                 120                 125

Cys Trp Ser Phe Ala Leu Thr Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Ser Cys Phe Asp Gly Lys Glu Trp Met His
            180                 185                 190

Val Cys Met Thr Gly Asn Asp Asn Asp Ala Ser Ala Gln Ile Ile Tyr
        195                 200                 205

Gly Gly Arg Met Thr Asp Ser Ile Lys Ser Trp Arg Lys Asp Ile Leu
    210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp Tyr Arg Val Tyr
                245                 250                 255

Trp Ile Arg Glu Gly Lys Ile Ile Lys Tyr Glu Asn Val Pro Lys Thr
            260                 265                 270

Lys Ile Gln His Leu Glu Glu Cys Ser Cys Tyr Val Asp Ile Asp Val
        275                 280                 285

Tyr Cys Ile Cys Arg Asp Asn Trp Lys Gly Ser Asn Arg Pro Trp Met
    290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
                325                 330                 335

Asp Ser Pro Ser Asn Val Asn Gly Gly Pro Gly Val Lys Gly Phe Gly
            340                 345                 350
```

```
Phe Lys Ala Gly Asp Asp Val Trp Leu Gly Arg Thr Val Ser Thr Ser
        355                 360                 365

Gly Arg Ser Gly Phe Glu Ile Ile Lys Val Thr Glu Gly Trp Ile Asn
    370                 375                 380

Ser Pro Asn His Val Lys Ser Ile Thr Gln Thr Leu Val Pro Asn Asn
385                 390                 395                 400

Asp Trp Ser Gly Tyr Ser Gly Ser Phe Ile Val Lys Ala Lys Asp Cys
                405                 410                 415

Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
        435                 440                 445

Leu Asp Asn Glu Pro Gly Ser Gly Asn Trp Pro Asp Gly Ser Asn Ile
    450                 455                 460

Gly Phe Met Pro Lys
465

<210> SEQ ID NO 9
<211> LENGTH: 4
<212> TYPE: PRT
<213> ORGANISM: Influenza A virus

<400> SEQUENCE: 9

Arg Arg Lys Lys
1
```